United States Patent

(12) United States Patent
McClanahan et al.

(10) Patent No.: US 7,294,327 B2
(45) Date of Patent: Nov. 13, 2007

(54) MULTI-STAGE CRYOGENIC ACID GAS REMOVAL

(75) Inventors: Timmons S. McClanahan, Florence, AL (US); Michael C. Crim, Florence, AL (US)

(73) Assignee: Tennessee Valley Authority, Knoxville, TN (US)

( * ) Notice: Subject to any disclaimer, the term of this patent is extended or adjusted under 35 U.S.C. 154(b) by 0 days.

(21) Appl. No.: 11/384,279

(22) Filed: Mar. 21, 2006

(65) Prior Publication Data

US 2007/0221541 A1    Sep. 27, 2007

(51) Int. Cl.
*C01B 17/027*    (2006.01)
(52) U.S. Cl. .................. 423/578.1; 62/617; 62/619; 518/700; 518/702; 518/704
(58) Field of Classification Search ............... 518/700, 518/702, 704; 423/578.1; 62/617, 533
See application file for complete search history.

(56) References Cited

U.S. PATENT DOCUMENTS

| | | | |
|---|---|---|---|
| 3,001,373 A | | 9/1961 | Eastman et al. |
| 3,074,245 A | | 1/1963 | Becker |
| 3,349,571 A | | 10/1967 | Nebgen |
| 3,544,291 A | | 12/1970 | Schlinger et al. |
| 3,614,872 A | | 10/1971 | Tassoney et al. |
| 4,378,048 A | | 3/1983 | Madgavkar et al. |
| 4,609,388 A | * | 9/1986 | Adler et al. .................. 62/632 |
| 4,957,515 A | | 9/1990 | Hegarty |
| 4,977,745 A | * | 12/1990 | Heichberger .................. 62/619 |

OTHER PUBLICATIONS

Gas Purification, fifth edition, 1997 A. Kohl et al., pp. 746-747.
Eugene Rosenbaum; Physical Chemistry 1970; pp. 550-552.
Haldor Topsoe, Combustion catalysts designed as the CK/CKM class, brochure cove r sheet and pp. 2-8, no date.
Journal of Chemical and Engineering, Apr. 1968; pp. 168-171, the date is a bit unclear.

* cited by examiner

Primary Examiner—Yvonne Eyler
Assistant Examiner—Sudhakar Katakam
(74) Attorney, Agent, or Firm—Sughrue Mion Pllc.

(57) ABSTRACT

A relatively simple and energy efficient multiple stage cryogenic process for the purification of a hydrogen-rich stream by the removal of acid gases, mainly $CO_2$ and $H_2S$, by method of autorefrigeration and delivering or producing those acid gases, mainly $CO_2$, at pressure sufficiently high for disposal by containment, commonly known as sequestration. Autorefrigeration is comprised of (a) condensing acid gases from the syngas stream by cooling the syngas, (b) separating the liquefied acid gases from the syngas, and (c) evaporating the liquefied acid gases at a pressure lower than that of the syngas to provide cooling. The process is composed of multiple autorefrigeration stages to generate multiple acid gas product streams with a pressure as high as practical in each stream so as to lessen the power needed to pressurize the acid gas streams for sequestration. The final autorefrigeration stage utilizes an antifreeze liquid that allows the final stage to operate below the freezing point of $CO_2$; thus allowing more acid gas removal. The antifreeze liquid is an alcohol or a mixture of alcohols with a freezing point lower than about minus 110 degrees F. and a boiling point higher than about 100 degrees F. The process includes hydrogen recovery and recycle as well as recovery of the energy contained in the sulfur bearing compounds. The process is especially well suited for $CO_2$ removal/sequestration from a coal (or petroleum coke) gasification process.

42 Claims, 3 Drawing Sheets

Autorefrigeration

Autorefrigeration with Antifreeze Circulation

MULTI-STAGE CRYOGENIC ACID GAS REMOVAL

BACKGROUND OF THE INVENTION

1. Field of the Invention

This invention relates to the separation of gases. More particularly, it relates to purification of a hydrogen-rich stream by the removal of acid gases, $CO_2$, $H_2S$, and COS, by the method of autorefrigeration. Further, this invention relates to a method for avoiding the emission to the atmosphere of $CO_2$, a so-called greenhouse gas. In a highly preferred embodiment, it relates to the production of $CO_2$ at a pressure sufficiently high for disposal by containment, a method commonly known as sequestration. The sequestration method itself is not a part of this invention.

2. Description of the Prior Art

There is increasing concern about combustion of fossil fuels worldwide because of the emission of carbon dioxide. Atmospheric $CO_2$ is believed capable of producing a "greenhouse effect" by trapping radiated heat from the earth's surface, thereby contributing to global warming. Although emission of $CO_2$ to the atmosphere is not yet regulated, the issue is one of fast rising political concern that future regulation is a strong possibility and worthy of new technology and invention to address the problem. It has been proposed in many technological forums that a way to limit the emission of $CO_2$ from fossil fuels is to utilize the energy in the fossil fuel to make hydrogen, which emits only water vapor when combusted. During hydrogen production, the carbon in the fossil fuel is converted to $CO_2$. Under current proposals, the $CO_2$ is then separated from the hydrogen and compressed to a high pressure for disposal. The high pressure is necessary for carrying out the most commonly proposed method of disposal: sequestration by deep underground or deep ocean containment. Although many commercial processes are available to produce purified hydrogen and $CO_2$, the energy consumed by undertaking both the separation process and the $CO_2$ compression process is quite high, making current processes economically unattractive. Our invention proposes a process to greatly decrease this energy consumption.

The processes for making hydrogen from fossil fuels are well-known. One broad class of these processes is gasification, in which a carbonaceous fuel (e.g., coal) is partially oxidized at high temperature and elevated pressure in the presence of water vapor to form mainly carbon monoxide (CO) and hydrogen ($H_2$). Then by the well known water-gas shift conversion reaction, the carbon monoxide is reacted with water vapor over a catalyst to form additional hydrogen and carbon dioxide. Sulfur in the fossil fuel is converted mainly to hydrogen sulfide during gasification. The hydrogen is then purified to remove $CO_2$ and $H_2S$ by a well known process method commonly called acid gas removal (so named because the compounds $CO_2$ and $H_2S$ will ionize in water to form mildly acidic solutions).

There are numerous methods for acid gas removal. Most commercially-applied processes use some form of solvent that has an affinity for acid gases. The solvents vary broadly and include chemical substances such as monoethanolamine in water, chilled methanol, or hot potassium carbonate ionized in water. The reference book *Gas Purification*, fifth edition, lists more than a dozen solvent-based processes into acid gas removal. Typically, the acid gases are absorbed into the solvent in an absorption tower to form a solvent stream rich in acid gases. Acid gases are then removed from the rich solvent by some combination of flashing at reduced pressure, stripping with a medium of nitrogen or steam, and/or distillation of the solvent. The solvent, now lean with respect to acid gases, is then returned to the absorption tower.

A chief drawback to these solvent-based acid gas removal processes is that a significant quantity of energy, either in the form of steam or electricity, is required to regenerate the solvent. The very act of diluting the acid gases within a solvent means that significant energy is required to reconstitute the acid gases as a pure stream. This energy penalty is made worse if the acid gases must be pressurized for sequestration. The pressure lost during flashing of the solvent at a reduced pressure must then be restored by compression of the acid gases. Even further energy must be expended if the $H_2S$ must be separated from the $CO_2$ prior to sequestering the $CO_2$ (an issue which has yet to be settled by environmental regulation).

Our invention uses the well-known method of autorefrigeration to remove acid gases. With autorefrigeration, acid gases are condensed and separated from the hydrogen stream, and the condensed acid gas itself is used as the refrigerant for cooling. Autorefrigeration is a standard method found in the prior art for purifying many types of gases, including hydrogen. In general, however, where these patented processes differ from our invention, is that our invention uses a series of autorefrigeration stages to remove and capture acid gases at multiple pressure levels, thereby greatly reducing the energy needed to pressurize the acid gases to the desired pressure for sequestration.

Autorefrigeration has been previously patented as a method of acid gas removal. In U.S. Pat. No. 3,001,373, Eastman et al., 1961, a process is described in which the bulk portion of $CO_2$ is removed by autorefrigeration, followed by the use of a chilled solvent to absorb additional $CO_2$. The solvent is regenerated by stripping with air at atmospheric pressure. The portion of $CO_2$ removed from the solvent in this latter manner is diluted by air and thus is not suitable for recovery for later sequestration. The pure $CO_2$ portion collected during autorefrigeration is expanded to near atmospheric pressure to generate additional cooling for the process, thereby making this portion of the $CO_2$ less suitable for sequestration because of the high energy requirement needed for pressurization.

In U.S. Pat. No. 3,614,872, Tassoney et al., 1971, a process is described in which hydrogen is purified of acid gases in a single stage of autorefrigeration. The autorefrigeration step is carried out by condensing acid gases at a temperature a few degrees above the freezing point of $CO_2$ (about −70° F.). Our invention is quite similar in that it uses the same basic autorefrigeration process step. However, our invention is an advance over Tassoney in two ways. First, our invention employs more than one autorefrigeration stage, which greatly reduces the energy requirements for pressurization of the acid gas stream. Second our invention employs a novel concept of using an antifreeze liquid compound to permit autorefrigeration to take place at a temperature colder than the normal freezing point of $CO_2$. This allows more acid gas to be removed from the hydrogen stream than would be possible using Tassoney's process.

SUMMARY OF THE INVENTION

The present invention provides a continuous process for removing acid gases ($CO_2$, $H_2S$ and COS) from a stream containing hydrogen and acid gases, hereafter called syngas. The hydrogen stream obtained in accordance with the present invention, hereafter called purified syngas, is preferably of a purity suitable for commercial use, e.g., as a fuel for generating electric power in a combustion turbine. The removed acid gases in accordance with our invention are generated as multiple streams of acid gases, each stream having the highest pressure practicable so as to minimize to the extent practicable the power needed to compress the acid gas streams for conventional containment or sequestration means. Our invention employs autorefrigeration to remove acid gases from the syngas, wherein the syngas is cooled to condense the acid gases, which permits the liquefied acid gases to be separated from the syngas, and wherein the liquefied acid gases are evaporated to provide the cooling of the syngas. Although autorefrigeration itself is not new, our invention utilizes a novel sequence of autorefrigeration stages in which the syngas is cooled to successively lower temperatures and in which the liquefied acid gases are evaporated at successively lower pressures from the first stage in the sequence to the last stage in the sequence. By employing this approach, the evaporated acid gas streams are produced at multiple pressure levels, each stage having its own characteristic pressure level.

Accordingly, our invention in its simplest form is a continuous process for removing acid gases from a syngas comprising a sequence of at least two stages; each stage comprising the steps of (a) condensing acid gases from the syngas by cooling the syngas to produce liquefied acid gases, (b) separating the liquefied acid gases from the syngas, and (c) evaporating the liquefied acid gases to provide the cooling of the syngas in step (a), with each of the stages in the sequence cooling the syngas to a successively lower temperature as the syngas progresses from the first stage to the last stage, and each of the stages in the sequence evaporating the liquefied acid gases at successively lower pressures, thereby separately producing an acid gas product stream from each of the stages, with the last stage discharging a purified syngas.

For many of the anticipated applications of our invention, the syngas must be cooled in the last stage to a temperature below the freezing point of $CO_2$ (about $-70°$ F.) to obtain the desired purity of the purified syngas. For these applications, a further and more specific aspect of our invention provides a method of using an antifreeze liquid to prevent freezing in the last stage. With this method, the antifreeze liquid is circulated continuously through steps (a), (b), (c) and returns to mix with the syngas entering the last stage.

In accordance with the process of the present invention, the energy and therefore the cost of pressurizing the removed acid gases for conventional containment or sequestration means is greatly reduced. In particular, our invention has an advantage when the purified syngas is applied for the purpose of producing electric power, with the added requirement that the acid gases must be sequestered. Persons skilled in the art of engineering design will recognize after due calculations that our process consumes from the net generation of electric power less than half of that consumed by conventional solvent-type acid gas removal processes.

The starting syngas stream treated in accordance with the present invention can be from any source. The syngas should preferably have sufficient pressure and $CO_2$ content so as to exhibit a partial pressure of $CO_2$ of at least 200 psia, and preferably more than 60 mole percent of the combustible gases present will be hydrogen. More preferred limits for these parameters are 300 psia and 90 mole percent, respectively. We contemplate that the process of the present invention will find most practical application where the starting syngas is the product of gasification of a carbonaceous material. The carbonaceous fuel of greatest interest is coal because of its low cost and abundance as a fossil fuel. Also of great interest is petroleum coke, which is similar in composition to coal and also low in cost.

It is, therefore, the principal object of this invention to provide a process for removing acid gases from a syngas via condensation, separation, and evaporation of the acid gases in a series of multiple autorefrigeration stages and, as a result of using multiple stages, to generate multiple acid gas product streams at differing pressures.

Detailed objects of the invention are as follows:

An object of this invention is to provide a process for removing acid gases from a syngas. While the acid gases may be used for any purpose, a preferred aspect of the invention involves sequestering the acid gases.

A still further object of this invention is to generate the multiple acid gas product streams with a pressure as high as practicable in each acid gas product stream so as to lessen the power needed to pressurize the acid gas streams, most preferably for sequestration.

A further object of this invention is to provide a process method for using a circulation of antifreeze liquid to permit the last autorefrigeration stage in the series to function at a temperature below the freezing point of carbon dioxide, thereby increasing the quantity of acid gases which can be condensed out of the syngas.

A still further object of this invention is to provide a process method within each stage of autorefrigeration of recovering dissolved hydrogen in the condensed acid gases.

It is a further object of this invention to provide a process method of oxidation for converting the sulfur-bearing compounds in the removed acid gases to a less environmentally noxious form of sulfur, namely sulfur dioxide or sulfur trioxide.

It is a further object of this invention to capture the heat generated by oxidation of the removed acid gases as useful energy for a process external to this invention, such as generating steam to produce electric power.

It is a further and more specific object of this invention to have the capability of removing more than 90 percent of the moles of carbon dioxide from a syngas.

It is a still further and more specific object of this invention to have the capability of removing more than 98 percent of the moles of sulfur-bearing compounds from a syngas.

DETAILED DESCRIPTION OF THE INVENTION

Figure 1:
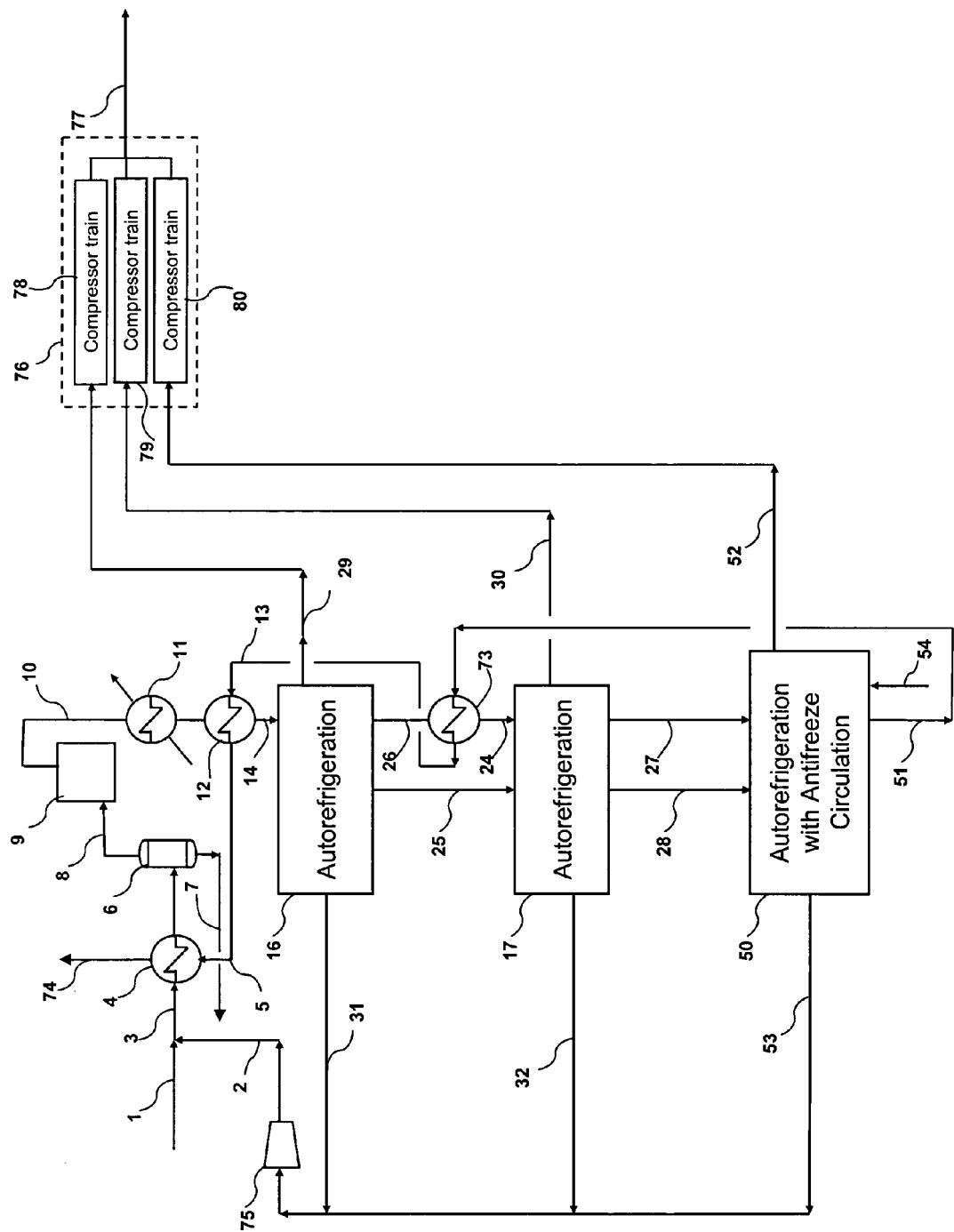
FIG. 1 is a general flow diagram showing all of the process methods employed by the preferred embodiment of our invention.

The following words and phrases are defined in the context of their use herein:

Acid gas or acid gases. The compounds $CO_2$, $H_2S$, and COS.

Acid gas product stream. A stream of acid gases leaving a stage.

Antifreeze liquid. A liquid substance miscible with liquefied acid gases which when added to liquefied acid gases lowers the freezing point of the liquefied acid gases (i.e., the mixture of liquefied acid gases and antifreeze liquid has a lower freezing point than the liquefied acid gases alone.)

Antifreeze mixture. A mixture of antifreeze liquid and liquefied acid gases.

Autorefrigerant. See liquefied acid gases.

Autorefrigeration. A three step process comprised of (a) condensing acid gases from the syngas stream by cooling the syngas, (b) separating the liquefied acid gases from the syngas, and (c) evaporating the liquefied acid gases to provide cooling of the syngas.

Autorefrigeration stage. See stage.

Combustibles or combustible gases. Any non-sulfur bearing syngas component which releases heat upon combustion with oxygen.

Dewpoint temperature. The hypothetical temperature at which water in the vapor phase first begins to condense as either a solid (ice) or a liquid.

Flash or flashing. An adiabatic process in which the pressure of a liquid stream is reduced (such as by flowing through a valve) and in which a portion of the liquid is vaporized.

Freezing. The formation of solids due to the cooling of a process stream, such solids being present in sufficient quantity to interfere with the process of our invention by the formation of blockages in streams or fouling of heat exchange surfaces.

Freezing point. The highest temperature at which solid formation begins in a process stream or a substance. For a pure substance, such as $CO_2$ or methanol, the freezing point is the triple point of the substance.

Hydrates. Solid compounds that contain water.

Liquefied acid gases (also called autorefrigerant). Acid gases from the syngas that have been condensed by cooling of the syngas.

Non-contact heat exchange. The transfer of heat from one process stream to another without direct physical contact of the two streams.

Normal boiling point. The temperature at which the vapor pressure of a substance is one atmosphere.

Partial pressure of $CO_2$. The mole fraction of $CO_2$ in the syngas multiplied times the total pressure of the syngas.

Pressurize. Any method of increasing the pressure of a process stream.

Purified syngas. The syngas leaving the last stage (stage N) and the syngas from that point forward in the process.

Sequester. To carry out a method of sequestration.

Sequestration. Any method of capturing and holding or utilizing carbon dioxide that requires elevated pressure of the carbon dioxide to function, such elevated pressure being greater than that of the highest pressure acid gas product stream as it leaves the first stage.

Stage. An element of our invention comprising the steps of (a) condensing acid gases from the syngas by cooling the syngas to produce liquefied acid gases, (b) separating the liquefied acid gases from the syngas, and (c) evaporating the liquefied acid gases to provide the cooling of the syngas in step (a). Our invention has at least two stages in sequence with each of the stages in the sequence cooling the syngas to a successively lower temperature as the syngas progresses from the first stage to the last stage, and each of the stages in the sequence evaporating the liquefied acid gases at successively lower pressures, thereby separately producing an acid gas product stream from each of the stages, with the last stage discharging a purified syngas. A further aspect of our invention provides a method of using an antifreeze liquid to prevent freezing in the last stage. With this method, the antifreeze liquid is circulated continuously through steps (a), (b), (c) and returns to mix with the syngas entering the last stage. A stage is also referred to as an autorefrigeration stage.

Starting syngas. A stream of hydrogen and acid gases entering our process which preferably has sufficient pressure and $CO_2$ content so as to preferably exhibit a partial pressure of $CO_2$ of at least 200 psia, and preferably more than 60 mole percent of the combustible gases present is hydrogen.

Syngas. A term used generically herein to include the starting syngas, the purified syngas, and the starting syngas which has had some portion of the acid gases condensed or removed by our process.

Unevaporated liquefied acid gases. The liquefied acid gases that remain after evaporation of liquefied acid gases in step (c) of a stage.

Unevaporated mixture. The mixture of antifreeze liquid and liquefied acid gases that remains after evaporation of the antifreeze liquid and liquefied acid gases in step (c) of a stage.

Figure 1A:
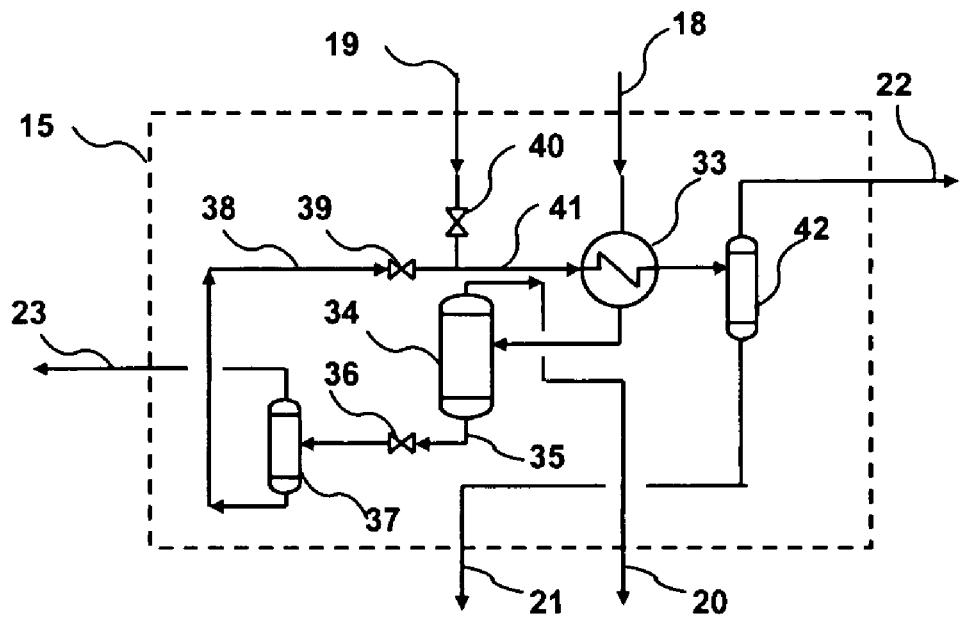
FIG. 1a is a flow diagram showing the details of an autorefrigeration stage.
Figure 1B:
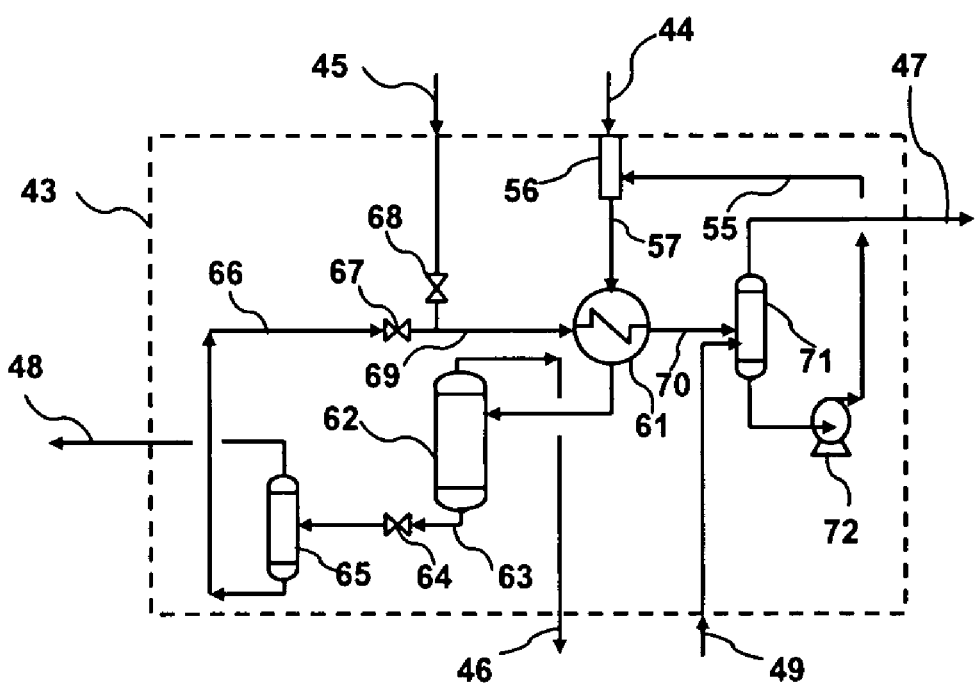
FIG. 1b is a flow diagram showing the details of an autorefrigeration stage modified to use a circulation of antifreeze liquid.

FIG. 1 together with the accompanying drawings, FIGS. 1a and 1b, illustrate the preferred embodiment of the present invention. Stream 1 is the starting syngas. Stream 1 preferably will contain more than about 60 mole percent of the combustible gases as hydrogen to be applicable for our invention. A hydrogen content of 90 mole percent or more of the combustible gases is more preferred. For purposes herein the terms combustibles or combustible gases are defined as any non-sulfur bearing syngas components which releases heat upon combustion with oxygen. Other than hydrogen, combustibles found in syngas typically include CO, methane and sometimes traces of other hydrocarbon compounds. As the hydrogen content of the syngas falls below 90 mole percent of the combustibles, the process of our invention would experience a gradual loss of efficacy for two reasons. First, as the hydrogen is replaced by other combustibles, with the primary replacement being CO because of the manner in which syngas is typically produced, less carbon is captured in the form of $CO_2$, preferably for sequestration. In other words, the CO remaining in the purified syngas will be later converted to $CO_2$ upon combustion and enter the atmosphere, an undesirable result. Second, the relatively higher boiling points of other combustibles compared with hydrogen can alter the operation of our process and make the operation more difficult because these combustibles are more easily condensed than hydrogen. At a level of combustibles of about 60 mole percent hydrogen or less, the operation reaches a point of being impractical and uneconomic due to partial condensation of these non-hydrogen combustibles during autorefrigeration and their permanent loss from the purified syngas. Considering all of the above, the combustibles in the starting syngas stream should preferably contain at least 60 mole percent hydrogen.

The starting syngas stream should have a pressure which provides a carbon dioxide partial pressure which enables the process of the present invention to be practiced with acceptable energy input in the form of electricity to compress the $CO_2$ for any desired purpose, which in a preferred embodiment will be sequestration. In this regard, we expect operation at a $CO_2$ partial pressure of 200 psia±20% will represent the lowest range of $CO_2$ partial pressures in the starting syngas stream which many users will find to offer acceptable, but marginal, process operation, especially as the partial pressure of $CO_2$ goes below 200 psia. A partial pressure of about 300 psia or higher is more preferred. Partial pressure of $CO_2$ is defined herein as it is defined for ideal gases, namely, the mole fraction of $CO_2$ in the syngas multiplied times the total pressure of the syngas. The maximum pressure of the syngas is theoretically unlimited except for the restraints imposed by the apparatus used in the process of the present invention, i.e., at extremely high syngas pressures there is the possibility of apparatus damage. This is a practical consideration which one of ordinary skill in the art will deal with using every day equipment principles.

The method of producing the starting syngas (stream 1) is any process for producing hydrogen that meets the above described limitations. Typical sources for the syngas are the well-known processes for gasifying or steam reforming of a carbonaceous fuel (e.g., coal, petroleum coke, oil, biomass, or natural gas). One method that we envision as being particularly attractive from a practical and economic standpoint is a slurry-fed, oxygen-fired, water quench coal (or petroleum coke) gasification process. An example of such a coal gasification process and one that is preferred for use by our invention is the coal gasification process originally patented in U.S. Pat. No. 3,544,291, December 1970, by Schlinger et al., assigned to Texaco, Inc., now commercially licensed by General Electric, Inc. (GE) in improved form. U.S. Pat. No. 3,544,291 is hereby incorporated by reference. The term slurry-fed refers to the mode of feeding coal to the gasifier. Finely ground coal and water are mixed to form a slurry which is pumped to the gasifier (i.e., the reactor vessel within the gasification process in which coal and oxygen are reacted) Pumping the coal as a slurry permits the gasifier to operate at a high pressure and, in turn, to produce syngas at a high pressure without having to compress the syngas. This pressure should typically be about 800 psia or higher to obtain the more preferred partial pressure of $CO_2$ of at least 300 psia. With current technology, the highest available pressure of syngas from a GE gasifier is about 1300 psia. If technological advances are made to safely and economically raise the highest available pressure, our invention will prove even more beneficial because the essential syngas property on which our invention relies is the partial pressure of the $CO_2$ in the syngas. With lower rank coals, which generate more $CO_2$ in proportion to hydrogen in the syngas, the partial pressure of $CO_2$ could range up to about 700 psia in a syngas with a total pressure of 1300 psia. Therefore, in summary, the starting syngas for our preferred embodiment has a pressure ranging from about 800 psia to 1300 psia and has a partial pressure of $CO_2$ ranging from about 300 psia to 700 psia. The term oxygen-fired means that a purified stream of oxygen, typically greater than 90 mole percent oxygen with the balance being substantially nitrogen and argon, is fed to the gasifier to partially oxidize the coal and convert it to gaseous components. The oxygen is typically produced by a method of air separation such as the cryogenic distillation of liquefied air. We prefer to use oxygen firing rather than air firing to avoid the dilution of the syngas with nitrogen which would otherwise lower the partial pressure of $CO_2$ in the syngas. The term "water quench" refers to the method of cooling the syngas after partial oxidation of the coal. The hot syngas is quenched directly in water which evaporates to produce a large proportion (>50 mole percent) of water vapor in the syngas. Water vapor promotes the shift reaction to convert CO and water to hydrogen and $CO_2$. The quench method is preferred for our invention because it is less expensive and much simpler than raising steam by indirectly cooling the syngas and then injecting the steam into the syngas. After gasifying a bituminous coal (such as Pittsburg #8) by the above described method and with subsequent shift conversion, the syngas will typically have a composition (molar dry basis) of about 57% $H_2$ and 40% $CO_2$, with the balance containing $H_2S$, COS, methane, nitrogen, argon and traces of many other components as are well known in the art. Typically, the components other than combustibles or acid gases are less than 2 mole percent of the starting syngas. Nitrogen and argon are the major components in this category. The main drawbacks of their presence are that they dilute the combustibles in the final product (i.e., purified syngas) and that they reduce the partial pressure of CO2 in the starting syngas, also by dilution. Therefore, we prefer that the other components are less than 10 mole percent of the starting syngas with less than 2 mole percent being more preferred.

It is anticipated that the sulfur containing species in the syngas will be handled in one of two ways. With one method, the starting syngas is received having been desulfurized after the gasification process to remove the sulfur species to an environmentally acceptable level. The acid gas recovered by our invention in this case is nearly pure $CO_2$ (typically about 99 mole percent $CO_2$ with typically about 0.01 mole percent to 0.05 mole percent as sulfur species and the balance trace amounts of other components). With a desulfurized starting syngas, the parameters of the process are selected in a manner to remove the amount of $CO_2$ desired by the user of our invention. With a second method, the sulfur species are not removed from the starting syngas before entering the process our invention. The parameters of the process are selected to remove the amount of sulfur desired by the user of our invention instead of $CO_2$. This is because requirements for syngas purity with respect to sulfur are very likely to be much more stringent than the requirements for $CO_2$. If the sulfur content of the coal or the blend of coal and petroleum coke used in the gasification process is very high, say about 10 weight percent, the content of sulfur species in the starting syngas will range up to about 2 mole percent. Therefore, the starting syngas for the preferred embodiment will have a sulfur content of about 2 mole percent or less. However, because our process is particularly effective at removing the sulfur species, a sulfur content of the syngas well in excess of 2 mole percent is acceptable. Starting with a syngas having a partial pressure of $CO_2$ of 300 psia or higher, our process is capable of removing 98 percent of the moles of sulfur in the starting syngas even if the starting syngas contains as much as about 10 mole percent of sulfur. The minimum sulfur content acceptable with our process is zero. The $CO_2$ content of the acid gas in the starting syngas, by difference from the sulfur species, is, therefore, preferably about 98 to 100 mole percent for the preferred embodiment and about 90 to 100 mole percent for the broad embodiment. Because the CO2 is by far the major component in the acid gas portion of the syngas, it is sometimes useful herein to refer to the properties of $CO_2$ or the quantities of $CO_2$ to explain the function of our process.

For purposes of describing the preferred embodiment, it is assumed that the sulfur in the syngas is not removed during syngas production. In other words, the sulfur is removed by the process of our invention and is sequestered along with the $CO_2$. The practice of our invention is essentially the same as that described below for FIGS. 1, 1*a*, and 1*b* whether or not sulfur is present in the syngas.

It is also assumed for the preferred embodiment that syngas stream 1 has a temperature in the range of about 80°

F. to 120° F. having been cooled, if needed, by external means well known in the art such as an industrial cooling water supply (not shown on the figures). (Wherever herein a numerical range is preceded by the word "about", such as the phrase "about 80° F. to 120° F.", it shall be understood that both the lower and upper limit given are approximate. Of course, any approximate range given herein also includes as part of that approximate range the precise range, e.g., about 80° F. to 120° F. would include and describe 80° F. to 120° F.) A temperature for the starting syngas of less than about 80° F. down to a practical minimum of about −40° F. is acceptable and would be preferable (because less external refrigeration would be needed). It is expected that the syngas will be saturated with water vapor due to the manner in which the syngas is produced, but a water vapor content less than saturated is acceptable and would also be preferable (because less cost associated with water removal would be incurred). In a similar fashion, no water vapor need be present for the operation of the present invention, but the large scale syngas production methods usually will involve the presence of water vapor in the syngas as a consequence of the manner in which the syngas is produced. With most anticipated applications of our invention, the syngas will be dried and cooled before the syngas enters stage 1 (i.e., the first stage, or stage 16 as shown on FIG. 1). By the phrase "before the syngas enters stage 1" wherever stated herein, we mean anywhere along the path of flow of the syngas from the starting syngas (syngas stream 1 on FIG. 1) to the entrance of the first autorefrigeration stage (syngas stream 14 on FIG. 1). Our preferred method of drying and cooling is described below.

Syngas stream 3 is a mixture of syngas stream 1 and a recycled stream, recycle gas stream 2, which will be described later. Stream 2 is relatively small, comprising typically 2 percent or less on a molar basis of stream 3. Stream 2 could be zero percent if users of our invention choose not to recycle. Syngas stream 3 is cooled in pre-cooler heat exchanger 4 to within a range of about 35° F. to 60° F. for the preferred embodiment to condense a portion of the water vapor which remained after syngas production. The operating or design temperature chosen within this range must be sufficiently warm to avoid formation of hydrates that would foul the heat transfer surfaces of heat exchanger 4. Hydrates are solid compounds that contain water. The temperature at which hydrates form is a function of the syngas composition and pressure. In particular, the partial pressure of $CO_2$ affects the hydrate formation temperature. At a partial pressure of $CO_2$ of about 200 psia, the minimum pressure for good economic operation, the hydrate formation point is estimated to be about 35° F., hence the selection of about 35° F. as the minimum for the range. Some process designers could choose to use an inhibitor added to the syngas such as diethylene glycol to lower the hydrate formation point and the freezing point of the condensate to well below 30° F. This would lower the cost for desiccant use but would add the cost for recovering the inhibitor, and thus the use of an inhibitor is a design choice based on economics. Also, a selective $H_2S$ removal process, if employed by the user of our invention, will act as a drying step and will thus augment or replace the syngas drying steps described herein. The source of cooling in the preferred embodiment is purified syngas stream 5. Condensed water is separated from the syngas and removed in knock-out vessel 6. Condensate stream 7 is disposed or used externally. Partially dried syngas stream 8 is dried in drying process 9 to a dewpoint sufficiently low to prevent formation of ice or hydrate deposits downstream. This dewpoint is about −70° F., which is roughly the coldest temperature during cooling of the syngas in which no antifreeze is present. At points in the process where antifreeze is present, the antifreeze is expected to inhibit freezing of both water and $CO_2$. A −70° F. dewpoint temperature for water is easily obtained by many commercial drying processes well known in the art such as processes utilizing a regenerable or a non-regenerable desiccant.

The dried syngas (stream 10 in FIG. 1) is then optionally cooled to augment the cooling in the autorefrigeration stages downstream and thereby permit the process to cool the syngas in the last stage to the temperature desired by the user of our invention. Cooling acts to supplement the cooling of the syngas that takes place in the stages and represents a preferred aspect of the invention. For the broad embodiment, this cooling of the syngas may range from no cooling at all (for dried syngas at a very high $CO_2$ partial pressure or a very low temperature of stream 10) up to about 100° F. reduction in temperature (for a very low $CO_2$ partial pressure of stream 10). With the preferred embodiment, the range of cooling is about 20° F. to 80° F. for a reduction in temperature; the high end of this range being necessary for a starting syngas at the lower end of the range of partial pressure of $CO_2$ for the preferred embodiment (about 300 psia) and vice versa for the high end of the range (about 700 psia). With the preferred embodiment, this cooling step will liquefy a portion of the acid gases. (Users of our invention will find that for many applications of our invention, this portion will range from about 1 percent to 5 percent of the moles of the acid gases in the stream 10.) In the preferred embodiment, this cooling is provided in two steps: (1) refrigeration unit 11, which is a source of external refrigeration, and (2) heat exchanger 12, which utilizes purified syngas stream 13 as the cooling source. (By external refrigeration we mean any method, commercial or otherwise, of chilling a stream in the present process and rejecting the heat outside of our process. Chilling has its art accepted meaning of cooling.) Syngas stream 14 leaves heat exchanger 12 as a two-phase stream. During operation of the preferred embodiment of our invention, the cooling and therefore the amount of liquid condensed should be balanced considering two factors: If too little liquid is made, there will be insufficient cooling downstream causing the temperature of the purified syngas leaving the last stage to be too warm and thus causing the process to remove less acid gas than desired. If too much liquid is made, the excess liquid will accumulate in the last stage and cause the purified syngas to be cooler than desired. If the amount of the excess is small, then the accumulation will, in time, stop and a new equilibrium will be established with the purified syngas being cooler than desired. If the excess is large, however, the accumulation will continue indefinitely resulting in eventual disruption of the process. Therefore, operation of our process is carried out by ongoing monitoring of the balance between these two operational states, that is, by increasing the amount of liquid produced when warming occurs in the last stage and decreasing the amount of liquid produced when accumulation of liquid and excessive cooling occurs in the last stage. The preferred method of maintaining this balance is to increase or decrease the cooling by external refrigeration in refrigeration unit 11. Some users of our invention may choose to intentionally produce more liquid in this step than would be necessary to supplement autorefrigeration. This excess liquid is then removed from the process at one or more points downstream (not shown on FIG. 1) and pumped (rather than compressed) to sequestration. The preferred location to remove this liquid is after evaporation of the liquefied gases in the last stage that does not use antifreeze (specifically separator vessel 42 on FIG. 1a within autorefrigeration stage 17 on FIG. 1). This method is a variation of our process and is equivalent to our process in that the power saved by liquefying acid gases and not having to compress those gases (i.e., pumping them instead, which requires less power) is approximately offset by the extra power needed for refrigeration.

The process from this point forward can be described broadly as autorefrigeration in the form of a series of autorefrigeration stages. Autorefrigeration is a three step process comprised in its most basic form of (a) condensing acid gases from the syngas stream by cooling the syngas, (b) separating the liquefied acid gases from the syngas, and (c) evaporating the liquefied acid gases to provide cooling of the syngas. The presence of other compounds within the liquefied acid gases such as dissolved gases (e.g., hydrogen), or the presence of an added substance such as methanol to lower the freezing point, or the use of an intermediary stream to transfer heat from the condensing stream to the evaporating stream do not alter the fundamental fact that an autorefrigeration stage exists if the three basic steps (a), (b) and (c) are present. And if those three steps are present two or more times (i.e. two or more stages), such process is contemplated as being part of the present invention. An autorefrigeration stage is characterized by a temperature range at which condensation of acid gases takes place and the pressure at which evaporation of the liquefied acid gases takes place. The term autorefrigerant, used hereafter for brevity, is synonymous with the term "liquefied acid gases".

The primary acid gas components in syngas are $CO_2$, $H_2S$, and COS. For purposes of definition these three components are the only components considered herein as acid gases. In actual practice, syngas will usually contain traces of other acid gas components such as carbon disulfide. These traces do not affect the process of the present invention. The name acid gas is derived from their tendency to ionize in water forming a weak acidic solution. However, their acidity is not a factor in the present invention. The useful property that these three acid gas components have in common is that they each have a much higher boiling point than hydrogen at any given pressure. This property permits the acid gases to be condensed and separated from hydrogen gas. The terms acid gas or acid gases are used throughout this patent as a naming convention to refer to these components collectively. The name acid gas is retained even if the acid gas has been condensed and is no longer a gas. It will be clear from context where acid gas has been condensed and is no longer a gas.

Syngas stream 14, preferably having had some acid gases in the stream liquefied as earlier explained, enters the first stage of three total stages of autorefrigeration. This number of stages was selected to illustrate the preferred embodiment and for the example to be described later. In practice, the number of autorefrigeration stages employed by our invention is a practical and economic choice made by the user of our invention. More stages reduce the power needed for pressurizing the acid gas product streams but increase the cost of the equipment. Theoretically, the number of stages is unlimited. With 20 stages or more, the estimated reduction in power usage for a marginal addition of a stage is extremely small—less than 0.1 percent. Thus a hypothetical upper limit, meaning a limit beyond which essentially no further benefit of adding stages is obtained, is 20 stages. There is a rapidly diminishing return of energy savings as the number of stages is increased beyond five (less than about 3 percent savings for the marginal addition of a fifth stage). At least two stages are necessary, however, to fulfill the spirit of our invention, which has been described previously as the capture of acid gases at multiple pressure levels. Concurrent with the selection of the number of stages is the selection of the pressure at which each stage operates, i.e., the pressure at which the autorefrigerant evaporates within each stage to provide cooling, also called evaporating pressure. (Specifically, this is the pressure exiting valve 39 on FIG. 1a or exiting valve 67 on FIG. 1b as will be described later in greater detail.) The evaporating pressure of the final stage in the series is a design choice based on the quantity of acid gas to be removed. The lower the evaporating pressure, the colder the autorefrigerant will evaporate, the colder the syngas will be cooled, and the greater will be the quantity of acid gas removed from the syngas through condensation. For the last stage, the preferred range of evaporating pressures exiting valve 67 is about 3 to 8 percent of the initial partial pressure of $CO_2$ in syngas stream 1. This range of operation corresponds to about 90 to 95 percent removal of the moles of $CO_2$ and about 98.0 to 99.5 percent removal of the moles of sulfur from syngas stream 1. Users of our invention desiring less acid gas removal should preferably select a pressure for the last stage higher than the preferred range to reduce energy consumption by the process. The lowest evaporating pressure practical is about 6 psia, which corresponds to a saturated liquid temperature of about −140° F. The evaporating pressures for each of the stages should be selected with the general objective of finding the optimum combination of evaporating pressures to provide the best economics. In most cases, it is expected that for any given number of stages the lowest power use by the process will also provide, approximately, the best economics. Concurrent with the selection of the evaporating pressure for each stage is the corresponding selection of the temperature to which the syngas is cooled in each stage. If the number of stages is small, such as the minimum of two stages, the cooling of the syngas from the entrance of a stage to the exit of a stage will be large, typically within a range of about 20° F. to 80° F. in temperature depending on the application. If the number of stages is large, such as the hypothetical maximum of 20 stages, then the cooling of the syngas across a stage will be much smaller, possibly as low as about 2° F., again depending on the application. With the preferred embodiment, which has three stages, the cooling of the syngas across a stage will typically fall within a range of about 10° F. to 80° F., again depending on the application. This temperature selection is detailed in the discussion of the individual stages and the process parameters therein.

For most applications of our process, we expect that users of our process will seek to minimize power consumption for any given number of stages by operating our process as closely as practicable to the optimum combination of evaporating pressures for the stages. (When we use the term "minimize power consumption" in the context of the optimum combination of evaporating pressures, we mean minimizing power use in the limited way provided by changing the process evaporating pressures. However, further minimization could be obtained in ways commonly available to all types of power consuming processes such as increasing the surface area of heat exchangers.) Optimizing the process in such a way is an important feature and advantage of our process, but it is not essential to the practice of our invention. Users will find that our process can be operated significantly far from the optimum pressures, say ±20 percent; without incurring a significant increase in power consumption (significant being more than about a 5 percent increase). Moreover, even if the evaporating pressures are poorly selected, such that more than 5 percent power increase relative to the optimum is experienced, our invention will still be quite effective in efficiently removing and preferably sequestering acid gas compared with conventional solvent-type acid gas removal processes. Therefore, regardless of how and for what purpose a user of our invention selects the stage pressures, such user is employing our process if two or more stages are present operating at two or more evaporating pressures.

To determine the desired combination of evaporating pressures, one can use chemical engineering calculations based on knowledge well known in the art. However, we offer below some convenient alternative methods to shorten the process of determining the desired combination of operating pressures. We consider a satisfactory combination of evaporating pressures to be any combination in which the power use is within about 5 percent of that possible with the optimum combination. If users of our process choose to use 2, 3, or 4 stages, a satisfactory combination of evaporating pressures can be found empirically by making proper engineering calculations for a process design and then altering evaporating pressures for each stage in the design. The search process can be expedited by utilizing process simulation software widely used by those skilled in the art of process design such as ChemCAD®. Additionally, described below, is an alternative method of finding a satisfactory combination of pressures. This method uses Microsoft® Excel spreadsheet program software widely available on desktop computers. With this method, the search process can be done easily and quickly by those skilled in the art of spreadsheet programming. This method is particularly appropriate if users of our invention choose to use a large number of stages, such as five or more, because finding a satisfactory combination of evaporating pressures may become difficult and possibly very time consuming even with the advantage of process simulation software. The necessary variables and mathematical formulas to carry out this search process on an Excel spreadsheet are described below. The variables calculated in this spreadsheet should only be used as mathematical devices to calculate a satisfactory combination of evaporating pressures. In other words, they are not intended to replace variables determined by proper engineering calculations made by those skilled in the art of process design.

Let N=the number of stages.

Let the symbol i denote a stage number beginning with the first stage in the flow of the syngas (i=1) and continuing to the last stage (i=N).

Let F=the flow of $CO_2$ in the starting syngas in lb-mole/h.

Let Fi=the amount of $CO_2$ removed by condensation in stage i and equivalent to the amount of $CO_2$ evaporated in stage i, lb-mole/h (the evaporated and condensed amounts will not be exactly equal, but they are approximately equal).

Let Pi=the partial pressure of $CO_2$ in the syngas leaving stage i, psia.

Let $Pi_{-1}$=the partial pressure of $CO_2$ in the syngas leaving stage i-1 and entering stage i, psia. Note: $P_0$ is the partial pressure of $CO_2$ in the starting syngas.

Let Pevi=the evaporating pressure of the liquefied acid gases in stage i, psia. This will be the pressure leaving valve 39 on FIG. 1a or, if the stage employs antifreeze, valve 67 on FIG. 1b. (The calculation of the series of Pevi numbers is the purpose of this spreadsheet.)

Let Pseq=the sequestration pressure to which the acid gas product streams will be compressed for disposal, psia.

Let Ei=the power in kW required to compress the acid gas product stream leaving stage i from pressure Pevi up to pressure Pseq.

In one column of the spreadsheet, enter a starting value for Pevi for each stage as follows: For the last stage (i.e. Pevi, where i=N), the evaporating pressure is set according to how much $CO_2$ or $H_2S$ the user of our invention desires to remove from the syngas. This number is determined by making proper engineering calculations for a final detailed process design. For this spreadsheet exercise, a suggested estimate is to use 5 percent of the partial pressure of $CO_2$ in the starting syngas, i.e. $0.05*P_0$. Later, when a preliminary design is made, this spreadsheet exercise can be repeated to finalize the estimates for the evaporating pressures to be used in the final design. For all of the other Pevi values, enter rough estimates or simply enter 100 psia for every stage. These estimates will provide the initial values to begin the calculations.

In a second column of the spreadsheet calculate the partial pressure of $CO_2$ leaving each stage using the formula:

Pi=Pevi/D, where D is a proportional factor that allows for a temperature difference to exist across the heat exchanger of a stage. The smaller D is, the greater the temperature difference. A factor of 0.7 is a good estimate to use here. It will allow for about a 15° F. to 20° F. temperature difference to occur. Users of our invention should apply their own factor here to reflect how closely they expect to design the temperature difference across the exchanger. This temperature difference can be estimated by comparing the boiling point temperatures of pure $CO_2$ at the respective pressures, Pi and Pevi.

In a third column of the spreadsheet, calculate the amount of $CO_2$ removed from each stage according to the formula:

$$Fi=F*(Pi_{-1}-Pi)/P_0$$

In a fourth column of the spreadsheet, calculate the power required to compress the $CO_2$ removed from each stage to the sequestration pressure, Pseq, as follows:

Ei=Fi*R*T*ln(Pseq/Pevi)/3412, where R is the ideal gas constant 1.987 Btu/lb-mole ° R, T is the estimated average temperature in ° R that the acid gas product undergoes during compression, ln denotes the natural log function, and 3412 is a unit conversion constant in Btu/kWh to convert the result for Ei into the units kW. A suggested number for T is 580° R. (120° F.). The estimate of T will not affect the final outcome of the spreadsheet with regard to its main purpose, which is to estimate a value for Pevi for each stage. The estimate of T only affects the estimate of power needed for compression.

Underneath the fourth column, designate a cell to calculate the sum of Ei values for all stages. This sum is designated ΣEi and is the numerical value which this spreadsheet seeks to minimize by finding the optimum combination of Pevi numbers. The minimization of ΣEi is conducted using a special mathematical tool in Excel known as Solver. In the Solver window, select ΣEi as the cell to be minimized. Then select each of the cells individually in the first column of Pevi numbers (except the cell for the last stage, stage i=N, which remains fixed) as cells that are to be changed by Solver during the search for the minimum ΣEi. Solver also has a feature that allows the user to enter constraints so that a cell will not go outside designated boundaries during the search. It is suggested that this constraint feature be used for the Pevi value in the next to last stage, i.e. i=N−1. Here, the constraint can be used to make sure that the pressure selected by Solver does not enter a range that would permit freezing to occur in the stage. A suggested minimum constraint for this stage is 100 psia. Once the Solver window is programmed as just described, the user only needs to click "Solve" for Solver to make the necessary calculations.

The Pevi estimates provided by the spreadsheet will be sufficiently accurate for use in the final design of the process (i.e. within 5 percent of the minimum power) but users of our invention may also want to try designs that raise or lower the Pevi values proportionately to find an even better design for their application and their own plant design methods. Solver, by finding starting points for the Pevi values, reduces the number of trials needed for the final design to a practical number for any designer skilled in the art.

FIG. 1a presents the process details of a typical autorefrigeration stage. This figure represents the processes found within the first two autorefrigeration stages, stages 16 and 17, as shown on FIG. 1. Dashed line 15 designates the process boundaries of a typical stage, with streams 18 through 23 being inlet or outlet streams as shown. Stream 18 represents the syngas stream entering a typical stage and is thus representative of streams 14 and 24 on FIG. 1. Stream 19 is representative of a flow of unevaporated autorefrigerant received from the previous stage. In the case of autorefrigeration stage 16 which is the first stage, no previous stage exists so there is no corresponding stream represented by stream 19. Stream 19 represents only stream 25 on FIG. 1. Syngas outlet stream 20 represents streams 26 and 27. Unevaporated autorefrigerant stream 21 represents streams 25 and 28. (In some instances in which a stream flows directly from one autorefrigeration stage to the next, the stream will be represented by two streams from FIG. 1a. An example is stream 25, which is represented by both an inlet stream, stream 19, and an outlet stream, stream 21.) Acid gas product stream 22 represents streams 29 and 30. Recycle gas stream 23 represents streams 31 and 32.

Continuing with FIG. 1a, a typical autorefrigeration stage functions as follows. Syngas stream 18 is cooled in autorefrigeration heat exchanger 33 to condense a portion of the acid gases. Separator vessel 34 separates the liquefied acid gases from the partially purified syngas. (If an autorefrigeration stage is the last stage in the sequence, the syngas leaving that stage is referred to as purified syngas from that point forward in its flow through the process.) The syngas leaves the autorefrigeration stage boundary as stream 20. The liquefied acid gases, stream 35, also called autorefrigerant, are flashed through valve 36. The term flash (or flashing) means simply reducing the pressure of a liquid stream such that a portion of the liquid is vaporized. (For purposes of discussion and for the example herein, the flash is assumed to be adiabatic and the portion vaporized is calculated as that portion necessary to make the enthalpy of the streams before and after the flash equal.) The purpose of this flashing step is to recover most of the hydrogen in the autorefrigerant to be recycled back into the process (as will be described later). Two other combustibles, CO and methane, are also recovered in this flashing step. The pressure selected for this flashing step is based on maximizing the value of the recovered combustibles minus the cost of equipment and energy needed for recycling the recycle gas. We believe that most users of our invention will find that this maximization will occur at a flash pressure of about 25 percent to 50 percent of the starting syngas pressure. This range will typically recover about 50 to 90 percent of the moles of hydrogen in the liquefied acid gases (stream 35). Separator vessel 37 separates the recycle gas, stream 23, from the remaining autorefrigerant, stream 38. Autorefrigerant stream 38 is then flashed in valve 39 to a selected evaporating pressure, the pressure preferably being selected for each stage according to criteria of best economic performance as described previously. If any additional autorefrigerant is available from the previous stage via stream 19, it is flashed through valve 40 to mix with the autorefrigerant from valve 39 to form autorefrigerant stream 41. Most or the entire autorefrigerant stream 41 is evaporated in heat exchanger 33. The unevaporated portion of the autorefrigerant is separated out in separator vessel 42 and routed to the next stage as stream 21. The evaporated portion of the autorefrigerant leaves the boundaries of the autorefrigeration stage as acid gas product stream 22. The pressure of stream 22 is essentially the same as the evaporating pressure leaving valve 39 or is slightly less than the evaporating pressure leaving valve 39 because of pressure loss through heat exchanger 33 and vessel 42, such pressure loss being determined by the design of the equipment, which is common to the art. The evaporating pressure of a stage, which is the pressure leaving valve 39, sets the temperature of stream 41, which is the coldest point in the stage and thus the coldest theoretical temperature to which the syngas can be cooled to condense acid gas. The temperature of stream 41 will range broadly, with a typical temperature range being from about 20° F. to −70° F. depending on the user's selection of the evaporating pressure. The temperature to which the syngas is cooled (stream 20) will determine the amount of acid gas removed from the syngas by the stage. Stream 20 must be set relatively warmer than stream 41 for practical reasons of providing a temperature difference for heat transfer to occur in heat exchanger 33. The temperature difference between streams 41 and 20 is a design choice, which for most applications will range from about 5° F. to 30° F. For the broad embodiment, we expect stream 20 will range from about 50° F. to about −65° F. For the preferred embodiment, we expect stream 20 will range from about 15° F. to −65° F. We expect a temperature of about −55° F. is more preferred as the lower limit in order to avoid operating too close to the freezing point of the liquefied acid gases. In the actual practice of our invention a plant designer will use this choice of temperature difference to calculate the physical area required for heat transfer in heat exchanger 33. Then during operation, the selected evaporating pressures for the stages will set the operating characteristics of each stage including the portion of acid gases condensed in heat exchanger 33, the quantity of autorefrigerant evaporated in heat exchanger 33, and the quantity of the unevaporated portion of the autorefrigerant. The preferred maximum evaporating pressure leaving valve 39 is about 60 percent of the partial pressure of $CO_2$ in the starting syngas (stream 1). As this pressure increases much above 60 percent, gradually less and less evaporation occurs until a pressure is reached at which no evaporation is possible. For the broad embodiment, in which the starting syngas pressure is only limited by mechanical limitations of the equipment to safely handle high pressures, the highest practical evaporating pressure is about 800 psia. Above 800 psia, the evaporative cooling capability of $CO_2$ diminishes rapidly as the pressure approaches the critical pressure for $CO_2$ (1070 psia). The preferred minimum evaporating pressure is about the pressure corresponding to the freezing point of pure $CO_2$, or about 75 psia. For practical reasons of providing a margin of safety to avoid freezing conditions, a more preferred minimum is about 100 psia.

FIG. 1b presents the process details of an autorefrigeration stage that has been modified to include a circulation of antifreeze liquid inside the boundaries of the stage. This modified stage is needed whenever, in the absence of the antifreeze liquid, the temperatures within the stage are expected to produce freezing conditions for carbon dioxide. Such freezing would likely foul heat exchange surfaces and potentially plug flash valves and piping. The temperature at which freezing is expected to begin is about that of pure carbon dioxide, around −70° F. With most applications of our invention, a temperature of below −70° F. is needed to condense a sufficient portion of the acid gases to meet the objects of the invention. Only if the partial pressure of carbon dioxide in the original syngas stream is very high, on the order of 1000 psia or more, would it be possible to condense and recover more than 90 percent of the moles of carbon dioxide from the starting syngas without using temperatures below −70° F. in the process.

FIG. 1b represents the process of the third and final autorefrigeration stage on FIG. 1, i.e., stage 50. Similar to the description for FIG. 1a, dashed line 43 designates the process boundaries of the stage, with streams 44 through 49 being inlet or outlet streams as shown. These streams are respectively syngas inlet stream 44, unevaporated autorefrigerant stream 45, syngas outlet stream 46, acid gas product stream 47, recycle gas stream 48, and antifreeze liquid makeup stream 49. This latter stream is needed to provide makeup for the small amount of antifreeze liquid that is lost via evaporation into streams 46, 47, and 48. Streams 44 through 49 represent and correspond to the streams on FIG. 1, as follows: stream 44 represents syngas stream 27; stream 45 represents unevaporated autorefrigerant stream 28; stream 46 represents purified syngas stream 51; stream 47 represents acid gas product stream 52; stream 48 represents recycle gas stream 53; and stream 49 represents antifreeze liquid makeup stream 54.

Within the boundaries of autorefrigeration stage 43 there is a continuous circulating loop of antifreeze liquid in a mixture with liquefied acid gases. This loop, beginning with mixer 56, follows in order through process and equipment stream numbers 57, 61, 62, 63, 64, 65, 66, 67, 69, 61, 70, 71, 72, 55 and returning to mixer 56. (Heat exchanger 61 appears twice in this loop because the loop flows through both the condensing step and the evaporating step inside the heat exchanger.) The term antifreeze mixture is used herein to describe a liquid which contains both antifreeze liquid and liquefied acid gases. The term antifreeze liquid refers only to the substance within the circulating loop which has been added to lower the freezing point of the antifreeze mixture. Freezing point is the highest temperature at which solid formation begins in a process stream. In describing a stream within the circulating loop, the term antifreeze liquid flow or circulation rate may be used to refer to the flow of only the antifreeze liquid within the stream. (The required properties of the antifreeze liquid and its flow rate in the circulating loop are discussed later.) The circulating loop carries the antifreeze liquid through both the condensing and evaporating steps inside heat exchanger 61. Heat exchanger 61 functions to cool the syngas and condense liquefied acid gases, similar to the function of heat exchanger 33 in FIG. 1a except that antifreeze liquid is also present. During condensing of the liquefied acid gases, the acid gases are absorbed into the antifreeze mixture as they condense, thereby freezing is prevented. We expect that most users of our invention will use a form of non-contact heat exchange in which the condensing step and evaporating step is separated by a wall or walls through which heat flows from the condensing side of the wall to the evaporating side. With this means, the coldest points on the condensing side of the walls are along the surfaces of the walls. Therefore, we expect users of our invention will need to provide a physical means of directing the flow of the antifreeze mixture to coat the walls to block the formation of frozen solids on the surfaces of the walls which would inhibit the flow of heat across the walls. One method well known in the art is a falling-film exchanger, a general example of which is described in the textbook *Process Heat Transfer*, by Donald Q. Kern, 1950, pages 746-747. These pages are hereby incorporated by reference. With this type of exchanger, the condensing step takes place inside vertical tubes. The antifreeze mixture is first separated from the syngas (not shown on the figures) and then directed to flow over a weir surrounding each tube at the top of each tube and then to flow as a film down the inside wall of each tube. Another method of coating the tube walls is to use a device inserted within each of the tubes known commonly in the art of heat exchange as a twisted tape insert. The insert causes the flow through the tube to move in a spiral direction. This imparts a velocity lateral to the bulk flow direction of the two-phase mixture which causes liquid to impinge upon the exchanger surfaces. This method can be used with either vertical tube or horizontal tube designs. With the evaporating step inside heat exchanger 61, which provides the cooling for the condensing step, the coldest points occur inside the body of the antifreeze mixture as it evaporates and therefore no physical means of flow distribution is necessary to prevent freezing.

Continuing with FIG. 1b, a typical autorefrigeration stage with antifreeze circulation functions as follows. Syngas stream 44 enters autorefrigeration stage 43 where it is mixed with antifreeze mixture stream 55. Gas and liquid are intimately mixed in mixer 56 which produces thorough contact between the two phases such that the two phases are substantially in equilibrium. During mixing, a portion of the acid gases are absorbed by the antifreeze mixture and the absorption causes a warming of the two-phase mixture, stream 57. Here, by substantially in equilibrium, we mean stream 57 leaving mixer 56 is preferably warmed to within 2° F. of the equilibrium temperature. How closely the temperature approaches equilibrium is determined by the design of mixer 56, such design being common in the art of specifying process equipment. At theoretical equilibrium, the antifreeze mixture will be saturated with acid gases in solution. Therefore, the size of the portion of the acid gases absorbed is set by how closely the antifreeze mixture approaches equilibrium. This warming effect facilitates good heat exchange by increasing the temperature difference at the warm end of heat exchanger 61 (i.e., the end of the heat exchanger where stream 57 enters). Two-phase mixture stream 57 is cooled in autorefrigeration heat exchanger 61 to condense a portion of the acid gases. The antifreeze mixture within stream 57 absorbs the $CO_2$ and other gases into the body of the antifreeze mixture and thereby prevents the freezing of $CO_2$ as it condenses.

Separator vessel 62 separates the antifreeze mixture from the purified syngas. (If an autorefrigeration stage makes use of antifreeze circulation, it will be the last stage in the sequence, and therefore the syngas is referred to as purified syngas.) The purified syngas leaves the autorefrigeration stage boundary as stream 46. Antifreeze mixture stream 63 is flashed through valve 64. The purpose of this flashing step is to recover most of the hydrogen in antifreeze mixture stream 63 to be recycled back into the process. Two other combustibles, CO and methane, are also recovered in this flashing step. The pressure selected for this flashing step is based on maximizing the value of the recovered combustibles minus the cost of equipment and energy needed for recycling the recycle gas. We believe that most users of our invention will find that this maximization will occur at a flash pressure of about 25 percent to 50 percent of the starting syngas pressure. This range will typically recover about 50 to 80 percent of the moles of hydrogen in the liquefied acid gases (stream 63). Separator vessel 65 separates the recycle gas, stream 48, from the remaining antifreeze mixture, stream 66. Antifreeze mixture stream 66 is then flashed in valve 67 to a selected evaporating pressure, the pressure being selected to provide sufficient cooling of the syngas to remove the quantity of acid gases desired by the user. If any autorefrigerant is available from the previous stage via stream 45, it is flashed through valve 68 to mix with the antifreeze mixture from valve 67 to form autorefrigerant stream 69. Most of the liquefied acid gases within antifreeze mixture stream 69 are evaporated in heat exchanger 61 to produce stream 70, which is a two-phase mixture of antifreeze mixture and evaporated acid gases.

The unevaporated portion of the antifreeze mixture is separated out in separator vessel 71 and returned to mixer 56 via pump 72 to complete the circulating loop. The evaporated portion of the antifreeze mixture leaves the boundaries of the autorefrigeration stage as acid gas product stream 47. The pressure of stream 47 is essentially the same as the evaporating pressure leaving valve 67 or is slightly less than the evaporating pressure leaving valve 67 because of pressure loss through heat exchanger 61 and vessel 71, such pressure loss being determined by the design of the equipment, which is common to the art. A small portion of the antifreeze liquid evaporates during autorefrigeration and leaves the circulating loop within stream 47 and to a much lesser extent through streams 46 and 48. Fresh antifreeze liquid is added directly to the circulating loop to make up for this loss. The preferred point of addition for antifreeze makeup stream 49 is separator vessel 71. The evaporating pressure leaving valve 67, in combination with the circulation rate of the antifreeze liquid, sets the flash temperature of stream 69, which is the coldest point in the stage and thus the coldest theoretical temperature to which the syngas can be cooled to condense acid gas. The temperature of stream 69 will range broadly, with a typical temperature range being from about −70° F. to −140° F. depending on the selection of these parameters. The temperature to which the syngas is cooled (stream 46) will determine the amount of acid gas removed from the syngas by the stage. Stream 46 must be set relatively warmer than stream 69 for practical reasons of providing a temperature difference for heat transfer to occur in heat exchanger 61. The temperature difference between streams 69 and 46 is a design choice, which for most applications will range from about 5° F. to 30° F. For the broad embodiment, we expect stream 46 will range from about −65° F. to about −135° F. The above cited limits of −140° F. for stream 69 and −135° F. for stream 46 are practical limits preferred for our process. A temperature of −140° F. is about as low as practical when using methanol, the preferred antifreeze liquid, which has a freezing point of −143° F. Furthermore, to operate below −140° F., the evaporating pressure needed to obtain cooling in heat exchanger 61 falls below 6 psia into a realm of operation in which we believe the compressor train (compressor train 80 on FIG. 1) becomes too expensive and the energy requirement for compression too high. With the right choice of antifreeze liquid, such as ethanol, which has a freezing point of −173° F., operation below −140° F. is possible but we believe most users of our process will find such operation to be impractical. The evaporating pressure needed to operate our process at −173° F. is about 1 psia. For the preferred embodiment, we expect stream 46 will range from about −80° F. to −130° F. In the actual practice of our invention a plant designer will use this choice of temperature difference to calculate the physical area required for heat transfer in heat exchanger 61. Then during operation, the selected evaporating pressure in combination with the selected antifreeze circulation rate will set the operating characteristics of the stage including the portion of acid gases condensed in heat exchanger 61, the portion of antifreeze mixture evaporated in heat exchanger 61, and the quantity of antifreeze liquid evaporated. Because a stage modified for antifreeze circulation is always the last stage, the selected evaporating pressure leaving valve 67 is a design choice based on the quantity of acid gas removal desired by the user. The preferred range for this choice is about 3 percent to 8 percent of the partial pressure of $CO_2$ in the starting syngas (stream 1). For the preferred embodiment in which the partial pressure of $CO_2$ in the syngas ranges from about 300 psia to 700 psia, this range corresponds to about 9 psia to 56 psia. For the lower limit of the preferred partial pressure of $CO_2$ in the starting syngas, about 200 psia, the lower limit of this range is about 6 psia. The upper limit is about 75 psia, above which no freezing is expected to occur.

The circulation rate for the antifreeze liquid should be the lowest rate possible that avoids freezing at any point within the circulating loop. By operating at the lowest circulation rate possible, the selected evaporating pressure exiting valve 67 will be the maximum possible while still obtaining the desired removal of acid gases from the syngas. (This higher evaporating pressure, in turn, reduces the power for compressing the acid gases, the main purpose of our invention). Using a rate higher than the minimum is acceptable for operation, but there will be a steady increase in power consumption as the circulation rate is raised. The reason for this is fundamental to the properties of vapors dissolved in liquid solution. As the antifreeze circulation rate increases, the concentration of acid gases in solution in the antifreeze mixture decreases. With decreased acid gas concentration in solution, a lower pressure is needed to evaporate the acid gases at any given temperature (Raoult's law of the thermodynamics of solutions).

The minimum effective circulation rate for the antifreeze liquid should be determined and set based on the properties of stream 69. Stream 69 is the coldest point in the autorefrigeration stage and the point in the circulating loop where the molar ratio of antifreeze liquid to liquid $CO_2$ is very nearly the smallest. Both factors determine the rate of antifreeze liquid needed to avoid freezing.

The circulation rate of the antifreeze liquid can be calculated by first utilizing the general equation for freezing point conditions in ideal solutions (from *Physical Chemistry* by Eugene Rosenbaum, 1970, pages 550-552, hereby incorporated by reference.):

In $Xa = Ha_f(T-T_o)/RTT_o$ where, for our invention, $Xa$ is the mole fraction of $CO_2$ in stream 69; $Ha_f$ is the heat of fusion of $CO_2$, 3582 Btu/lb-mole; T is the temperature of stream 69 in °R, To is the freezing point of pure $CO_2$, 390° R; R is the ideal gas constant, 1.987 Btu/lb-mole°R. By entering a value for the temperature of stream 69 (T), the mole fraction of $CO_2$ in solution (Xa) at which freezing begins is calculated. The antifreeze liquid circulation rate is then determined as the minimum rate necessary to dilute the $CO_2$ in stream 69 to the calculated value of Xa. Because the value of T can range from about 320° R (−140° F.) up to the freezing point of pure $CO_2$, about 390° R (−70° F.), the value of Xa according to the above formula can range from about 0.36 up to 1 (pure $CO_2$). Essentially all of the remainder of the antifreeze mixture in stream 69 will be antifreeze liquid and therefore the antifreeze liquid in stream 69 will range from 0 to about 0.64 mole fraction. However, for practical reasons of assuring antifreeze protection during ordinary process fluctuations, we can say the range of antifreeze liquid for our process should be about 0.05 to 0.75 mole fraction in stream 69. Because the above equation is for ideal solutions, the actual circulation rate in practice will vary depending on the degree to which the solution in stream 69 varies from ideal. It is expected that in the practice of our invention, users will alter the antifreeze circulation rate as needed to keep the circulation rate as low as practicable while still avoiding freezing. Users of our invention may also find that some minor freezing in stream 69 can be tolerated if the frozen solids are slurried in stream 69 and thus do not produce blockages in the process equipment.

Broadly described, the antifreeze liquid may be any liquid substance which is capable of preventing freezing throughout the continuous circulating loop of the last autorefrigeration stage. In order to have this capability, we believe the antifreeze liquid should have certain properties as follows: The antifreeze liquid should preferably be a substance that is completely miscible with liquefied acid gases at the coldest temperature in the process, which occurs in stream 69. Preferably, the antifreeze liquid should have a freezing point lower than the coldest temperature in the process. (Note: it is possible for the antifreeze to have a freezing point above that of stream 69 because, just as the antifreeze liquid lowers the freezing point of the liquefied acid gases, the liquefied acid gases lower the freezing point of the antifreeze liquid.) For most applications of our invention the antifreeze should preferably have a freezing point of about −110° F. or lower. For operation at the preferred lower limit of application of our invention, the antifreeze should preferably have a freezing point less than about −140° F. There is no lower limit for the freezing point, which is to say, the freezing point of the antifreeze liquid cannot be too low to be acceptable for our process. The antifreeze liquid should preferably also have a relatively high normal boiling point. (By normal boiling point we mean the temperature at which the antifreeze liquid exhibits a vapor pressure of one atmosphere absolute.) The higher the normal boiling point, the less volatile the substance is, and therefore the less antifreeze liquid that will be lost through evaporation. (It is only the cost incurred through evaporative loss that makes the normal boiling point important to our invention.) Compounds with normal boiling points below about 100° F. are not likely to be good candidates for the choice of antifreeze liquid because of evaporative losses. Many organic compounds, particularly oxygenated organics, such as alcohols, ketones, and ethers, have properties in which the freezing point and normal boiling point are widely different. Liquid $CO_2$ is known to be a strong solvent for organic compounds and therefore is expected to be miscible with almost all organic compounds. Examples of organic compounds with acceptable freezing and normal boiling points are the alcohol ethanol, which has a freezing point below −170° F. and a normal boiling point above +170° F., methyl ethyl ketone (−124° F. freezing point and +175° F. normal boiling point) and dipropyl ether (−190° F. freezing point and +193° F. normal boiling point). The common industrial alcohols methanol, propanol, isopropanol, butanol, and isobutanol are all good candidates in that they have freezing points below −126° F. and normal boiling points well above +100° F. ChemCAD® computer models simulating the process of our invention show that all six of the above named alcohols produce similar process performance numbers (i.e., they all allow the process of our invention to remove about the same amount of acid gas with roughly the same energy input to the process). Any alcohol or mixture of alcohols with a freezing point less than about −110° F. and a normal boiling point above about 100° F. is expected to be acceptable as a choice of antifreeze liquid for most applications of our process. Based on our modeling of the above named alcohols, changing the alcohol compound will alter to a small degree the operating parameters but will not meaningfully change the performance of the process nor its capability of achieving the objects of the invention. Methanol is chosen as the preferred embodiment for our invention because it is relatively low in cost compared with other chemicals and because there is substantial industrial experience in the use of methanol as an absorbent for acid gases under refrigerated conditions. Methanol has a freezing point of about −143° F. and a normal boiling point of +148° F.

Returning to FIG. 1, purified syngas stream 51 is warmed by non-contact counterflow heat exchange with the syngas flowing between the stages to augment the cooling duty provided by autorefrigeration. In the preferred embodiment, this augmentation of cooling is illustrated by heat exchanger 73, which cools the syngas flowing between the first stage (stage 16) and the second stage (stage 17). Users of our invention might also choose to use the purified syngas to cool the syngas between the second and third stages (stages 17 and 50, respectively) before the purified syngas flows to heat exchanger 73. This is a design choice based on the economic considerations of adding an additional heat exchanger. In our preferred embodiment, we chose to not cool the syngas between the second and third stages because the temperature difference available for heat exchange is much less than that available in heat exchanger 73. Similarly, when more than three stages are chosen for the design, users may choose to cool the syngas at all of the points between stages or at fewer points depending on their own calculation of the economics.

The purified syngas then continues its flow path through heat exchangers 12 and 4, as previously described. Purified syngas stream 74 leaves the process of our invention as the final product for sale or for further application in an end-use process (such as combustion to generate power or as a source of hydrogen for chemical synthesis).

The recycle gas streams from all three autorefrigeration stages, streams 31, 32 and 53, are pressurized and recycled back to mix with syngas stream 1. If all of the recycle gas streams are collected before pressurizing and mixed together to form one stream, which is the preferred embodiment, then only one compressor, recycle compressor 75, as shown in FIG. 1, is needed. With this method, the flash pressures of the three recycle gas streams will be essentially the same (differing only by the difference in pressure loss between the point of each flash and the point where the streams are mixed, a typically negligible pressure loss). The compressed mixture of recycle gas streams, stream 2, is then mixed with starting syngas stream 1 to form syngas stream 3. If users of our invention choose not to generate recycle gas streams, then they may expect the purified syngas to contain typically 1 percent to 2 percent less moles of hydrogen than the starting syngas, i.e. about 1 to 2 percent hydrogen will be lost by exiting with the acid gas product streams (streams 29, 30, and 52). However, with the generation of recycle gas streams under the guidelines discussed earlier, the loss of hydrogen will be reduced to typically about 0.3 to 0.5 percent. Users of our invention may also expect that, when three autorefrigeration stages are used, typically most (greater than half) of the moles of hydrogen recovered for recycle will be recovered in the recycle gas stream from the first stage (stream 31) and that only a minor portion (typically 5 to 10 percent of the moles of hydrogen recovered) will be recovered in the recycle gas stream of the last stage (stream 53). The remainder, about 25 to 40 percent of the moles of hydrogen, will be recovered in the second stage.

It is a preferred aspect of our invention that the acid gas product streams, streams 29, 30, and 52, are pressurized to a pressure sufficient for sequestration of carbon dioxide. By the term sequestration, we mean any method of capturing and holding or utilizing carbon dioxide that requires elevated pressure of the carbon dioxide to function, such elevated pressure being greater than that of the highest pressure acid gas product stream as it leaves the first autorefrigeration stage (i.e., the pressure of stream 29). The method of sequestration itself is not a part of this invention. By the term sequester, we mean the verb form of sequestration, that is, to carry out a method of sequestration. For most applications of sequestration, such elevated pressure will exceed 1000 psia. Examples of sequestration by capturing and holding include underground storage (i.e., deep well injection) and deep ocean storage. An example of sequestration by utilization is to use pressurized carbon dioxide to increase production of crude oil from a natural reservoir, a method known in the art as enhanced oil recovery. The term pressurizing (or pressurize) is defined for purposes herein as any method of increasing the pressure of a process stream, such as pumping for liquids or compressing for gases. The selection of the method of pressurizing is a design choice to be based on practical considerations of operability and cost. Some designers may choose to compress each of the acid gas product streams independently using a multi-stage intercooled series of gas compressors and then mix the three compressed streams to form a final pressurized stream. If the sequestration pressure required is very high, say 2000 psia or higher, some designers may choose to independently compress the acid gas product streams to an intermediate pressure, mix them, condense the mixed stream by cooling to produce a liquid, and then pump the liquid to the final sequestration pressure. Process block 76 contains the process steps of pressurizing and mixing the acid gas streams to form final acid gas product stream 77 at a pressure suitable for sequestration. The preferred embodiment is compression of each of the three acid gas product streams in separate multi-stage, intercooled compressor trains. These three compressor trains are represented by process blocks 78, 79, and 80. The number of compression stages in each compressor train is a design choice.

An environmental issue which is yet to be resolved is whether or not the sulfur-containing compounds in the syngas are environmentally acceptable for sequestration. If declared unacceptable, the compounds can be removed from the syngas by employing the well-known method of selective acid gas removal during syngas production and our invention can still be applied for $CO_2$ removal and subsequent $CO_2$ sequestration. Selective acid gas removal processes are capable of removing a high percentage of sulfur compounds (>99 percent on a molar basis) while leaving most of the $CO_2$ (>75 percent on a molar basis) in the syngas. U.S. Pat. No. 4,957,515 describes one such process specifically for application to syngas and is hereby incorporated by reference. However, an alternative to selective acid gas removal, proposed herein as part of our invention, is to oxidize the sulfur-containing compounds in the acid gas product streams of our invention to a less environmentally noxious form of sulfur, that is, sulfur dioxide or sulfur trioxide. With the preferred embodiment, where the oxidation is carried out at temperatures ranging from about 300° F. to about 1000° F., a catalyst is used to promote the oxidation reactions.

Figure 2:
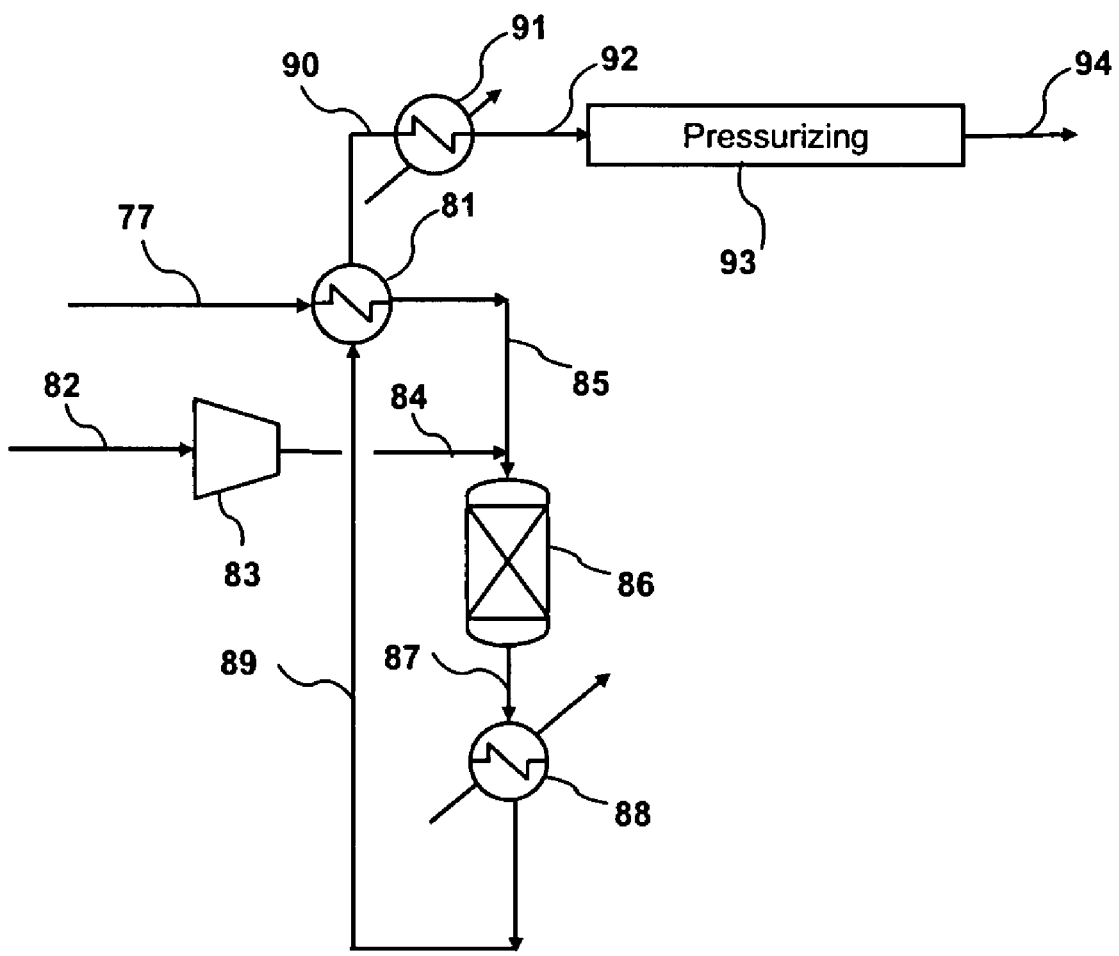
FIG. 2 is a flow diagram of a process, supplemental to the preferred embodiment, to oxidize and convert the reduced sulfur compounds in the final acid gas product stream to sulfur dioxide or sulfur trioxide and to transfer the heat of reaction to an external stream.

FIG. 2 is a drawing showing the preferred embodiment for our oxidation process. Stream 77 is the final acid gas product stream as was described previously for FIG. 1. Stream 77 is heated to a temperature of at least 300° F. in heat exchanger 81, the approximate minimum temperature needed to initiate the oxidation reactions. Higher preheat temperatures are preferred to increase the rate of these reactions. However, the preheat temperature is limited by the properties of the catalyst, as will be discussed later. Stream 82 is high purity oxygen. An oxygen content of greater than 90 mole percent oxygen is preferred. A lower oxygen content than 90 mole percent could be acceptable if the oxidation step and the sequestration method both can accept and function properly with the additional inert gases present in the high purity oxygen stream. With many applications of our invention, and in particular with applications of coal gasification as the syngas source, the high purity oxygen can be obtained from the same source as that used to provide oxygen for syngas production. As a result of compression for syngas production, stream 82 already has a pressure sufficiently high for feed to a coal gasifier. Compressor 83 further elevates the pressure of the oxygen to the pressure needed for mixing oxygen stream 84 with acid gas stream 85, which is the heated acid gas stream leaving heat exchanger 81. Oxidation reactor 86 contains a solid catalyst which promotes the combustion of sulfur-containing compounds and combustibles such as hydrogen, CO, and methane in the acid gas stream. The purpose of the catalyst is to lower the temperature needed for ignition, which, in turn, lowers the cost of the equipment and eliminates the need for supplemental fuel to achieve ignition temperature. Combustion catalysts are well-known in the art. Typically, combustion catalysts contain noble metals (e.g. platinum or palladium) or metal oxides. An example of a platinum-based catalyst patented for the purpose of combusting low heating value gases containing hydrogen sulfide is found in U.S. Pat. No. 4,378,048, Madgavkar, et. al, hereby incorporated by reference. Combustion catalysts are also available commercially. An example is the catalyst manufacturer Haldor Topsoe, which offers a product line of combustion catalysts designated as the CK/CKM class. The CK/CKM class offers catalysts that are capable of oxidizing sulfur-bearing compounds and catalysts that are sulfur tolerant for oxidizing other combustibles, both types being appropriate for our process. A typical maximum operating temperature for the catalyst is about 900° F. to 1000° F. This maximum, in turn, sets the maximum temperature for preheating the syngas and is based on the total heating value of all the combustibles in the acid gas stream. For instance, when using a coal feedstock with a typical value of 3.5 weight percent sulfur, the acid gas feed to the reactor (stream 85) will have a low heating value of typically about 125 Btu/lb, most of which is due to the $H_2S$ present. Preheating stream 85 to 550° F., for example, yields a final temperature of typically about 980° F. in stream 87 after combustion of all $H_2S$ present to $SO_2$. Therefore, a temperature of 550° F. is a good choice for the preheat temperature in this case.

The quantity of oxidant added via stream 82 is based on the needs for the combustion process. The preferred form of combustion is to add sufficient oxygen to convert essentially all of the $H_2S$ and COS to $SO_2$ (and the other combustion byproducts, water and $CO_2$). The reaction thermodynamics are quite favorable in that essentially all of the oxygen is theoretically consumed even if a rather large 200° F. approach to equilibrium is allowed. As those skilled in the art are aware, the "approach to equilibrium" is the chemical equilibrium of the combustion reactions theoretically calculated at a temperature 200° F. higher than the maximum temperature in oxidation reactor 86. Since the combustion reaction is exothermic, using a higher temperature for the equilibrium calculations than the actual temperature will predict less oxygen being reacted.

Further addition of oxidant is theoretically possible which converts $SO_2$ to $SO_3$ with some additional release of heat. However, this is considered less practical in that SO3 can react with water in the gas phase to form sulfuric acid, which is expected to be highly corrosive to heat exchanger 81. Also, the additional heat released is relatively small compared with the initial reaction to make $SO_2$ and may not justify economically the additional oxygen requirements. Nevertheless, combustion to make SO3 is a valid, but less preferred, design choice.

Stream 87 leaving oxidation reactor 86 is cooled in heat exchanger 88 to transfer the desired amount heat of reaction as useful heat to an external process stream within the end-use process for the hydrogen. (By the term "external process stream," we mean a process stream not described herein as part of our process or a stream leaving the process of our invention.) For instance, if the purified hydrogen is to be used for the generation of electric power in a combined cycle, the heat from heat exchanger 88 could be used to preheat the purified hydrogen stream, or it could be used to generate high pressure steam for use in a steam turbine. The percentage of the heat of reaction captured as useful heat is a design choice based on economics (i.e. the value of that useful heat versus the cost of capturing it). About 75 to 95 percent is the preferred range for this percentage.

Stream 89 is cooled in heat exchanger 81 as it heats stream 77. Depending on the temperature, pressure, and water content of stream 90 as it exits heat exchanger 81, stream 90 may contain water condensate. This condensate is expected to be mildly acidic (pH>2) and therefore should not be a particularly difficult problem for selection of materials in heat exchanger 81. If stream 90 is too warm to be acceptable for sequestration, it is further cooled in heat exchanger 91 by an external cooling source (e.g., cooling water). If stream 92 exiting heat exchanger 91 has sufficient pressure for sequestration, acid gas stream 92 is routed directly to sequestration without benefit of further pressurizing (pressurizing step 93) as shown in FIG. 2. Other design choices allow for carrying out oxidation at a pressure lower than that needed for sequestration and then pressurizing stream 92 using a compressor train for step 93 to yield the needed pressure for stream 94. As a further option, heat exchanger 91 could function as an external source of refrigeration to condense all of stream 92 into a liquid and then the pressurizing step 93 is applied as a pump. Similarly, as a design choice, oxidant stream 82 may be fed to the oxidation process in the form of a liquid. In this case the liquid is pumped to the needed pressure and some of the heat from stream 89 is used to vaporize the liquid. Stream 94 is referred to as the final oxidized acid gas product stream to distinguish it from stream 77, the final acid gas product stream.

EXAMPLE

In order that those skilled in the art may better understand how the present invention can be practiced, the following example is given by way of illustration only and not necessarily by way of limitation, since numerous variations thereof will occur and will undoubtedly be made by those skilled in the art without substantially departing from the true and intended scope and spirit of the instant invention herein taught and disclosed.

Pressures, temperatures, compositions, flow rates and other stream properties presented in the example below were calculated using ChemCAD® process simulation software, a product of Chemstations, Inc. headquartered in Houston Tex. Collectively these calculations are referred to herein as a computer simulation model or simply as a model. The software version used was CC-Steady State, version 5.3. ChemCAD® is a computer simulation program widely used throughout the chemical process industry and considered to be state of the art. As with any software simulation, the numerical results are estimates based on equations of state and other predictive equations. The numerical results effectively illustrate the principles of our invention and its purpose and intent when applied.

Most of the software calculations are routine chemical engineering calculations. An exception to this is that the vapor-liquid equilibria for hydrogen and $CO_2$ are non-ideal and therefore an equation of state must be selected that best predicts this non-ideality. Experimental data collected within the pressure and temperature range of interest was obtained from a 1966 experimental investigation of liquid-vapor equilibria conducted by J. O, Spano, et. al. for the University of Colorado and published in the Journal of Chemical and Engineering Data (1968), pages 168-171, hereby incorporated by reference. The equation of state known as Extended Soave-Redlich-Kwong (specifically, the TSRK calculation of thermodynamics in ChemCAD) matches this experimental data with reasonable accuracy. For instance, at a pressure and temperature of 1063 psia and −45° F., well within the range of interest for our invention, the saturated vapor phase has an experimental $CO_2$ content of 16.8 mole % compared with 17.8 mole % predicted by TSRK. It should be noted that the TSRK predictions are considered conservative and therefore well-suited for presenting process results that are attainable in practice. This is because at any given pressure and temperature at which autorefrigeration takes place, TSRK predicts slightly less $CO_2$ will be condensed than would be predicted by the experimental data. (Ideal system calculations would predict 12.4 mole %, a large error compared to experimental and decidedly not conservative if used in a simulation.) The TSRK equation of state also includes special calculation methods for $CO_2$ dissolved in methanol, and therefore TSRK is particularly appropriate for predicting the properties of the antifreeze mixture in the final autorefrigeration stage.

Syngas stream 1 is typical of syngas streams produced by the gasification of coal. A computer simulation model of coal gasification was used to estimate the properties of stream 1. The modeled method of syngas production is a slurry-fed, oxygen-fired, water quench coal gasification process with two added shift reactors to convert more than 97 percent of the moles of CO from the gasifier to hydrogen and $CO_2$. Flow rates and other process conditions for syngas production provided herein are selected to give context to the source of syngas stream 1, and are known in the art as syngas production per se is conventional. The oxidant is composed of 95 mole percent oxygen. The coal used by the gasification model is a common industrial bituminous coal with the designated name Pittsburgh #8. Pittsburg #8 has a dry ultimate analysis comprising in weight percent: C—73.4, H—5.0, S—3.5, N—1.4, ash—11.5, O—5.2 (by difference) and has a measured high heating value when combusted of 13,313 Btu/lb. The flow rate of coal is 2400 tons/day of dry coal. Heat input as coal is 2663 million Btu/h (780 MW). The gasifier operates at a temperature of about 2400° F. and a pressure of about 1150 psia. Syngas stream 1 has a total pressure of 1110 psia, a temperature of 105° F., and has a partial pressure of $CO_2$ of about 446 psia, which exceeds the preferred level of 300 psia. Pressure loss is a factor well known in the art and actually can be ignored for purposes of illustrating our invention. A 10 psi pressure loss of the syngas as it flows through the process equipment is a typical pressure loss in the system of the type illustrated, and is simply given for completeness. For simplicity, this pressure loss was assumed to occur at the beginning of the process. The hydrogen content as a percent of combustibles is 98 mole percent, which well-exceeds the preferred level of 90 mole percent. Syngas stream 1 has a composition and component flow rates as shown in Table I. The total of all three acid gas components ($CO_2+H_2S+COS$) is 11,796 lb-mole/h. This is the combined amount of acid gas our invention targets for removal in this example and is referred to below as "total moles of acid gases."

TABLE I

|  | Stream 1, syngas | | Stream 3, syngas plus recycle gas | |
| --- | --- | --- | --- | --- |
|  | Mole % | Lb-mole/h | Mole % | Lb-mole/h |
| $H_2$ | 56.56 | 16,292 | 56.42 | 16,498 |
| $CO_2$ | 40.20 | 11,578 | 40.33 | 11,793 |
| $H_2S$ | 0.71 | 204 | 0.71 | 207 |
| COS | 0.05 | 14 | 0.05 | 14 |
| $H_2O$ | 0.14 | 39 | 0.13 | 39 |
| CO | 0.78 | 223 | 0.78 | 229 |
| $CH_4$ | 0.20 | 57 | 0.20 | 59 |
| $N_2$ | 0.65 | 188 | 0.66 | 192 |
| Ar | 0.71 | 205 | 0.72 | 211 |

Table I also shows stream 3, which is a mixture of stream 1 plus recycle gas (stream 2) recycled from the autorefrigeration stages. Stream 3 is cooled from 105° F. to about 50° F. in heat exchanger 4 by countercurrent indirect cooling with purified hydrogen stream 5. Stream 5 is about −29° F. as it enters heat exchanger 4. The chosen temperature of 50° F. is intended to be sufficiently warm to prevent formation of solid hydrates and to keep ice from forming on the exchanger walls due to indirect contact with stream 5. In practice, this temperature may be slightly warmer or colder as determined by operating experience. If a warmer temperature is needed, the energy consumption of the process in the form of electricity will be slightly higher than described in this example (less than a 2 percent increase for every 10° F. increase). Water condensate, about 513 lb/h, is collected in knock-out vessel 6. (A use for this water condensate is to recycle it back to syngas production to be used as makeup water for the syngas quench.) Syngas stream 8 still contains about 194 lb/h of water vapor, which is essentially completely removed by solid desiccant in drying process 9 to a water dewpoint less than −70° F.

Stream 10, having been dried, is then cooled in heat exchangers 11 and 12 to condense about 3 percent of the moles of acid gases prior to entering the autorefrigeration stages. Heat exchanger 11 removes about 11.7 million Btu/h from the syngas using Freon R-22 as an external refrigerant source. Estimated electric power consumption for the refrigerant system is 1.24 MW. Heat exchanger 12 removes an additional 2 million Btu/h using purified syngas stream 13 (−45° F.) as the cooling source. Syngas stream 14 leaving heat exchanger 12 has a temperature of +4.5° F. and contains about 3 percent of total moles of acid gases in a liquid state. The temperature of stream 14 should be controlled during operation by adjusting the amount of cooling in refrigeration unit 11. This adjustment is made to provide sufficient liquid needed for the cooling in the stages downstream but not so much liquid as to cause an unacceptable accumulation of liquid in the final stage or excessive cooling of the purified syngas leaving the final stage.

For the description of the first two autorefrigeration stages, stages 16 and 17, FIG. 1a is referenced to describe the internal operation of each stage. Inlet and outlet streams on FIG. 1a are also cross referenced to their corresponding streams on FIG. 1 by providing both stream numbers.

Referring to autorefrigeration stage 16, syngas stream 18, 14 is cooled in heat exchanger 33 to −15° F. by autorefrigeration. About 37 percent of total moles of acid gases are condensed in this step. To obtain the desired temperature of −15° F. in stream 20, 26 leaving the stage, the temperature of stream 41 is preferably colder than −15° F. to provide reasonably sufficient temperature difference across the tube walls of heat exchanger 33. An evaporating pressure of 210 psia downstream of valve 39 is selected to cool autorefrigerant stream 41 to a temperature of −30° F. for this purpose. The pressure of 210 psia was chosen to minimize, approximately, the total power required for pressurization in all of process block 76. After gas/liquid separation in vessel 34, syngas stream 20, 26 leaves the stage having been enriched from about 56 mole percent hydrogen to about 67 mole percent hydrogen. Autorefrigerant stream 35, which is predominately $CO_2$, contains about 1 percent of the moles of hydrogen present in the starting syngas (stream 1). About 80 percent of this hydrogen is recovered for recycling by flashing the autorefrigerant in valve 36 to a pressure of 400 psia and separating out recycle gas stream 23, 31 in vessel 37. About 4 percent of the moles of $CO_2$ in stream 35 are also vaporized into the recycle gas stream. The pressure of 400 psia is a design choice which takes into consideration, for instance, that more hydrogen is recovered at a lower flash pressure but more electric power is consumed by the overall process. Autorefrigerant 38 is then flashed in valve 39 to a pressure of 210 psia, which yields an autorefrigerant with an initial boiling point of about −30° F. (Since this is the first autorefrigeration stage in the sequence, stream 19 has no flow and valve 40 is not needed.) The autorefrigerant warms slightly as it is evaporated in heat exchanger 33 to a temperature of about −18° F. After separation in vessel 42, acid gas product stream 22, 29 has a flow rate of about 4500 lb-mole/h and is composed of about 96 mole percent $CO_2$ and about 3 mole percent $H_2S$. The unevaporated autorefrigerant, stream 21, 25, which has a flow of about 160 lb-mole/h, is routed to the next autorefrigeration stage in the sequence (stage 17).

Syngas stream 20, 26 is further cooled in heat exchanger 73 from −15° F. to about −21° F. using purified syngas stream 51 as the cooling source. About 8.5 percent of total moles of acid gases are condensed by this cooling, which provides the extra autorefrigerant needed for both the second stage, stage 17, and the final stage, stage 50.

Referring to autorefrigeration stage 17, syngas stream 18, 24 is cooled in heat exchanger 33 to −55° F. by autorefrigeration. Because stage 17 is the last stage in the sequence that can operate without benefit of antifreeze, it operates at the coldest temperatures practical, which is about −55° F. for the syngas and about −65° F. for the autorefrigerant evaporating at the chosen evaporating pressure of 100 psia. The reasoning behind this is that autorefrigeration without antifreeze is the most energy efficient method of removal. Therefore it is beneficial to condense and remove as much acid gas as possible before employing the antifreeze. After gas/liquid separation in vessel 34, syngas stream 20, 27 has been enriched from about 67 mole percent hydrogen as it leaves stage 16 to about 83 mole percent hydrogen as it leaves stage 17. Autorefrigerant stream 35, which is predominately $CO_2$, contains about 0.6 percent of the moles of hydrogen in the starting syngas. About 70 percent of this hydrogen is recovered for recycling by flashing the autorefrigerant in valve 36 to a pressure of 400 psia and separating out recycle gas stream 23, 32 in vessel 37. About 1 percent of the moles of $CO_2$ in stream 35 are also vaporized into the recycle gas stream. Autorefrigerant stream 38 is then flashed in valve 39 to a pressure of 100 psia, which yields an autorefrigerant with an initial boiling point of about −65° F. Stream 21, 25, which is the unevaporated autorefrigerant from the previous stage, enters stage 17 and is now designated as stream 19, 25. Stream 19, 25 is flashed in valve 40 to 100 psia and is mixed with the flash stream from valve 39 to produce autorefrigerant stream 41, which has a pressure of 100 psia and a temperature of −65° F. The autorefrigerant warms slightly as it is evaporated in heat exchanger 33 to a temperature of about −56° F. After separation in vessel 42, acid gas product stream 22, 30 has a flow rate of about 4100 lb-mole/h and is composed of about 97 mole percent $CO_2$ and about 1.3 mole percent $H_2S$. The unevaporated autorefrigerant, stream 21, 28, which has a flow of about 538 lb-mole/h, is routed to the next autorefrigeration stage in the sequence (stage 50).

It is instructive at this point to examine how the results of this example would appear when using only these first two autorefrigeration stages in the process. In this case, stream 27 becomes the purified syngas stream and is applied as the cooling source in heat exchanger 73. No unevaporated autorefrigerant is produced in stream 28. Otherwise operating conditions are nearly or exactly the same as described above. The first two autorefrigeration stages combined remove about 76 percent of total moles of acid gases and about the same percentage of the moles of $CO_2$ in the starting syngas. If the sulfur had been removed from the syngas initially during syngas production, a removal percentage of 76 percent could quite possibly be, depending on the future of environmental law, adequate for sequestration of $CO_2$. In such a case, no additional autorefrigeration stages would be needed. The first two stages also remove about 93 percent of the moles of sulfur in the starting syngas, which may not be acceptable under current environmental law for combustion of a fuel gas in a new process. However, by choosing to add a third autorefrigeration stage with novel antifreeze circulation, our process can increase the removal of moles of sulfur in the starting syngas to over 98 percent. And, with only the marginal cost of including a third stage with a compressor train, the rather high cost of a sulfur removal process in the syngas production area is avoided. Thus, the operating conditions for the third stage, as described below, are based upon a high target percentage for sulfur removal (99 percent of the moles of sulfur in the starting syngas in this example). As an added benefit, the third stage also increases the moles of $CO_2$ removal from the starting syngas to a figure above 90 percent.

For the description of the third autorefrigeration stage, stage 50, FIG. 1b is referenced to describe the internal operation. Inlet and outlet streams on FIG. 1b are also cross referenced to their corresponding streams on FIG. 1 by providing both stream numbers.

Syngas stream 44, 27 is mixed with antifreeze mixture stream 55 in mixer 56, which for this example is an in-line static mixing device well known in the art of chemical processing. The antifreeze liquid in stream 55 is methanol. The two phase mixture stream 57 exiting mixer 56 has been warmed slightly to about −38° F. due to absorption of acid gases into the liquid phase. (The initial streams are both colder than −38° F.: stream 44, 27 is about −55° F.; stream 55 is about −41° F.) Acid gases in the syngas portion of stream 57 condense and are absorbed into the liquid. Stream 57 enters heat exchanger 61 where acid gases are condensed and join the antifreeze mixture. The liquid and vapor leaving heat exchanger 61 are at an equilibrium temperature of −95° F. This temperature is a process parameter chosen to provide at least 99 percent removal of the moles of sulfur from the starting syngas. Purified syngas stream 46, 51 leaving separator vessel 62 contains about 2 lb-mole/h total sulfur ($H_2S+COS$), representing a 99.1 percent removal of the moles sulfur from the starting syngas. The purified syngas also contains about 945 lb-mole/h of $CO_2$, which represents a 92 percent removal of the moles of $CO_2$ from the starting syngas. In total, purified syngas stream 51 has been enriched to about 91 mole percent hydrogen as it leaves stage 50. Antifreeze mixture stream 63 contains about 0.1 percent of the moles of hydrogen in the starting syngas. About 65 percent of this hydrogen is recovered for recycling by flashing the antifreeze mixture in valve 64 to a pressure of 400 psia and separating out recycle gas stream 48, 53 in vessel 65. About 1 percent of the moles of $CO_2$ in stream 63 are also vaporized into recycle gas stream 48, 53. Antifreeze mixture stream 66 is then flashed in valve 67 to a pressure of 30 psia. Stream 21, 28, which is the unevaporated autorefrigerant from the previous stage, enters stage 50 and is now designated as stream 45, 28. Stream 45, 28 is flashed in valve 68 to 30 psia and is mixed with the flash stream from valve 67 to produce antifreeze mixture stream 69, which has a pressure of 30 psia and a temperature of −103.6° F., coldest temperature point in the process. In stream 69, the flow rate of antifreeze liquid is 1260 lb-mol/h and the total flow of antifreeze mixture is 3768 lb-mol/h. Preferably, the flow rate of antifreeze liquid in stream 69 is controlled by controlling the flow of stream 55 as it leaves pump 72. In stream 55, the flow rate of antifreeze liquid is 1260 lb-mol/h and the total flow of antifreeze mixture is 1382 lb-mol/h. The mole fraction of liquid $CO_2$ in stream 69 is 0.65 corresponding to a freezing point of −103.6° F. for an ideal solution. During operation, if a lower freezing point temperature were desired, the flow of stream 55 would be increased. The antifreeze mixture warms as it is partially evaporated in heat exchanger 61 to a temperature of about −43° F. (stream 70). After separation in vessel 71, acid gas product stream 47, 52 has a flow rate of about 2400 lb-mole/h and is composed of about 98 mole percent $CO_2$ and about 1 mole percent $H_2S$. Fresh methanol is added via stream 49, 54 directly into vessel 71 to make up for evaporative losses of methanol and to maintain a sufficient supply of methanol in circulation throughout the circulating loop. Preferably, this is done by adjusting the flow of stream 49, 54 to maintain a prescribed level in vessel 71, a method common in the art of process operation. Evaporative losses of methanol are estimated to be 2 lb-mole/h. Stream 49, 54 will equal evaporative losses during steady state operation.

The purified syngas leaving the last autorefrigeration stage (stream 51) is warmed in heat exchangers 73, 12, and 4, as previously described, and then leaves the process as the purified syngas product stream 74. Table II shows the estimated pressure, temperature, and composition of stream 74.

TABLE II

| | Stream 74, purified syngas product | |
|---|---|---|
| Pressure, psia | 1100 | |
| Temperature, ° F. | 88 | |
| Composition | Mole % | Lb-mole/h |
| $H_2$ | 91.10 | 16227 |
| $CO_2$ | 5.30 | 945 |
| $H_2S$ | 0.01 | 1.9 |
| COS | 0.0005 | 0.1 |
| $H_2O$ | 0 | 0 |
| CO | 1.22 | 217 |
| $CH_4$ | 0.27 | 48 |
| $N_2$ | 1.03 | 184 |
| Ar | 1.07 | 190 |

Table III shows the estimated pressure, temperature, and composition of the three acid gas product streams (streams 29, 30, and 52). For purposes of discussion and identification, these three streams and their corresponding autorefrigeration stages are designated high pressure (HP), medium pressure (MP), and low pressure (LP), respectively.

TABLE III

| | Stream 29, HP acid gas product | | Stream 30, MP acid gas product | | Stream 52, LP acid gas product | |
|---|---|---|---|---|---|---|
| Pressure, psia | 210 | | 100 | | 30 | |
| Temperature, ° F. | −18 | | −56 | | −43 | |
| Composition | Mole % | Lb-mole/h | Mole % | Lb-mole/h | Mole % | Lb-mole/h |
| $H_2$ | 0.64 | 29 | 0.73 | 30 | 0.27 | 6 |
| $CO_2$ | 96.33 | 4309 | 97.47 | 3985 | 97.94 | 2339 |
| $H_2S$ | 2.58 | 115 | 1.30 | 53 | 1.42 | 34 |
| COS | 0.19 | 9 | 0.07 | 3 | 0.10 | 2 |
| $CH_3OH$ | 0 | 0 | 0 | 0 | 0.08 | 2 |
| Other | 0.26 | 11 | 0.43 | 17 | 0.19 | 5 |
| Totals | 100.00 | 4473 | 100.00 | 4088 | 100.00 | 2388 |

Each of the acid gas product streams are compressed separately using systems of multi-stage intercooled compressors called compressor trains. The number of compressor stages employed was 3, 4, and 5, respectively, for the HP, MP, and LP acid gas product streams. For intercooling it is assumed that the compressed syngas is cooled to 95° F. between compressor stages. All three acid gas product streams are compressed to 1595 psia and then mixed to form final acid gas product stream 77. A pressure of 1595 psia (110 bar) has been used in some past studies of gasification with $CO_2$ sequestration, and thus it is adopted for this example to provide comparison of our invention with other processes. Stream 77 is detailed in Table IV.

TABLE IV

| | Stream 77, final acid gas product | |
|---|---|---|
| Pressure, psia | 1595 | |
| Temperature, ° F. | 158 | |
| Composition | Mole % | Lb-mole/h |
| $H_2$ | 0.59 | 65 |
| $CO_2$ | 97.11 | 10632 |
| $H_2S$ | 1.85 | 203 |
| COS | 0.12 | 14 |
| $CH_4$ | 0.08 | 9 |
| $CH_3OH$ | 0.02 | 2 |
| Other | 0.23 | 24 |
| Totals | 100.00 | 10949 |

Table V presents the key measures of the performance of our invention in this example. To calculate estimates for electric power consumption, all compressors and pumps were assumed to have an adiabatic efficiency of 80 percent and an electric motor efficiency of 95 percent.

TABLE V

| | |
|---|---|
| Percent of moles of $CO_2$ removed from the starting syngas | 91.8 |
| Percent of moles of sulfur removed from the starting syngas | 99.1 |
| Percent of total moles of acid gas evaporated in the HP stage (stage 16; 210 psia) | 37.6 |
| Percent of total moles of acid gas evaporated in the MP stage (stage 17; 100 psia) | 34.3 |
| Percent of total moles of acid gas evaporated in the LP stage (stage 50; 30 psia) | 20.1 |
| TOTAL | 92.0 |

TABLE V-continued

Summary of electric power consumption

| | |
|---|---|
| Refrigerant system for heat exchanger 11 | 1.24 MW |
| HP compressor train 78 | 2.81 MW |
| MP compressor train 79 | 3.62 MW |
| LP compressor train 80 | 3.55 MW |
| Recycle compressor 75 | 0.16 MW |
| Pump 72 | 0.07 MW |
| TOTAL electric power consumption | 11.45 MW |
| MW of electric power consumption per MW of heat input as coal . . . | 1.47 percent |

Table V helps to illustrate the advantage of using multiple stages of autorefrigeration. This can be seen, for instance, by comparing the performance of the HP stage with the LP stage. Almost twice as much acid gas is evaporated by the HP stage as by the LP stage (37.6% vs. 20.1%, respectively), yet the power consumed by the HP compressor train is significantly less than that of the LP compressor train (2.81 MW vs. 3.55 MW, respectively).

Most illustrative of the overall advantage of our invention is the final figure in the table of 1.47 percent, which expresses the proportion of electric power consumed by our process compared with the heat input as coal. Persons skilled in the art of using coal gasification to make electric power will readily recognize that the proportion of power consumed by conventional solvent-type acid gas removal systems to do the same degree of hydrogen purification is on the order of 4 percent or higher. (To be more precise in the use of terminology, the term "power consumption" in the case of conventional acid gas removal means the sum of electric power consumed plus the amount of electric power which could have been produced by the steam consumed.)

As a point of comparison, the above example was recalculated on the basis of initially producing the syngas with a lower total pressure (747 psia) and the minimum preferred level of partial pressure of $CO_2$ (300 psia). To obtain the minimum desired removal of moles of carbon dioxide in the starting syngas of 90 percent, the syngas was cooled in the final stage of autorefrigeration (stage 50) to a lower temperature, −102° F. rather than −95° F., and correspondingly the evaporating pressure was lowered from 30 psia to 25 psia. Other operating parameters were adjusted as needed consistent with the principles of our invention described herein. The quantity of sulfur removed was 99 percent of the moles of sulfur in the starting syngas, which met the desired minimum. The total electric power required increased significantly to 13.84 MW from 11.45 MW. This comparison demonstrates that our invention can meet desired targets for acid gas removal even with a lower pressure syngas, but also demonstrates that there is a significant benefit to producing the syngas at higher pressure.

As another point of comparison, the example was recalculated using four autorefrigeration stages rather than three used in the example. Syngas stream 1 had the same composition shown in Table I and the same pressure (1110 psia total pressure with 446 psia partial pressure of $CO_2$). The last stage of the four stage model used the same operating parameters as the last stage in the example, that is, 30 psia evaporating pressure and −95° F. syngas temperature. This ensured that the molar removal of $CO_2$ and $H_2S$ from the starting syngas was essentially the same as the example (91.8 percent and 99.1 percent, respectively). The parameters of the other three stages were selected so as to minimize, approximately, the total power use. Total electric power required by the four stage model was 11.17 MW versus 11.45 MW for the example, a reduction of only about 2.5 percent.

If future environmental laws permit the sequestration of reduced sulfur compounds ($H_2S$ and COS), then the above example presents a complete illustration of how our process could be applied to purify hydrogen. However, our process also provides for a process of oxidation aided by a catalyst to convert the reduced sulfur compounds to the oxidized compound $SO_2$ which is less noxious from an environmental standpoint. Referring to FIG. 2, stream 77 has a composition and flow rate given previously in Table IV for the final acid gas product stream. The anticipated pressure drop in oxidation reactor 86 due to the presence of a catalyst should be taken into account, so stream 77 is compressed to a slightly higher pressure (1610 psia vs. 1595 psia) and has a very slightly higher temperature (159° F. vs. 158° F.). The additional power for this compression is so small (0.03 MW) that it does not meaningfully alter any previously stated power consumption numbers. After heating in heat exchanger 81, stream 85 has a temperature of 550° F. The oxidant, stream 82, having been compressed by the same compressor that delivers oxidant to the coal gasifier enters the process at a pressure of 1350 psia. Table VI shows details for both stream 77 and stream 82.

TABLE VI

| | Stream 77, final acid gas product | | Stream 82, oxidant | |
| --- | --- | --- | --- | --- |
| Pressure, psia | 1610 | | 1350 | |
| Temperature, ° F. | 159 | | 340 | |
| | Mole % | Lb-mole/h | Mole % | Lb-mole/h |
| $H_2$ | 0.59 | 65 | | |
| $CO_2$ | 97.11 | 10632 | | |
| $H_2S$ | 1.85 | 203 | | |
| COS | 0.12 | 14 | | |
| $CH_4$ | 0.08 | 9 | | |
| CO | 0.06 | 6 | | |
| $CH_3OH$ | 0.02 | 2 | | |
| $O_2$ | | | 95.0 | 381 |
| $N_2$ | 0.03 | 4 | 1.5 | 6 |
| Ar | 0.14 | 15 | 3.5 | 14 |
| Totals | 100.00 | 10950 | 100.0 | 401 |

Stream 82 is compressed in compressor 83 to yield oxidant stream 84 with a pressure of 1610 psia and a temperature of 390° F. Streams 84 and 85 are mixed and reacted in oxidation reactor 86. A commercial combustion catalyst that promotes oxidation of sulfur compounds (e.g., CK/CKM class combustion catalyst offered commercially by Haldor Topsoe, Inc.) is used. Even allowing for a large approach to equilibrium of 200° F., essentially all of the $H_2S$ and COS are converted to $SO_2$ (and also converted to the other respective oxidation products, water and $CO_2$.) Essentially all oxygen in the oxidant is reacted. The other combustibles present—hydrogen, CO, methane, and methanol—are likewise reacted and essentially all converted to the combustion products water and $CO_2$. Stream 87 emerges from reactor 86 with an estimated temperature of 982° F. The heat of reaction was 59.5 million Btu/h. Cooling of stream 87 in heat exchanger 88 to 600° F. provides about 52.6 million Btu/h (88 percent of the heat of reaction) of high level heat for making high pressure steam or heating the purified syngas if desired for the end-use process for the hydrogen (such as combustion in a combustion turbine). Stream 89 with a temperature of 600° F. provides the heat needed for preheating the incoming acid gas in heat exchanger 81. Stream 90 emerges from heat exchanger 81 at a temperature of 209° F. At this temperature a large portion of the water vapor from combustion condenses to a weak acidic liquid with a pH of about 2.4. The oxidized acid gas is further cooled in heat exchanger 91 to 105° F. (This cooling step may or may not be needed for sequestration but cooling is assumed for this example.) Pressurizing step 93 is not needed for this example since the final pressure of 1595 psia meets the assumed requirements for sequestration. The final oxidized acid gas product stream, stream 94, is detailed in Table VII.

TABLE VII

Stream 94, final oxidized acid gas product

| Pressure, psia | 1595 |
| --- | --- |
| Temperature, °F. | 105 |
| Mole percent liquid | 2.5 |

|  | Mole % | Lb-mole/h |
| --- | --- | --- |
| $H_2$ | <0.0001 | <1 |
| $CO_2$ | 95.14 | 10663 |
| $H_2S$ | <0.0001 | <1 |
| COS | <0.0001 | <1 |
| $CH_4$ | <0.0001 | <1 |
| CO | <0.002 | <1 |
| $CH_3OH$ | <0.0001 | <1 |
| $H_2O$ | 2.58 | 290 |
| $O_2$ | <0.0001 | <1 |
| $SO_2$ | 1.93 | 216 |

TABLE VII-continued

Stream 94, final oxidized acid gas product

| Pressure, psia | 1595 |
| --- | --- |
| Temperature, °F. | 105 |
| Mole percent liquid | 2.5 |

|  | Mole % | Lb-mole/h |
| --- | --- | --- |
| $N_2$ | 0.09 | 10 |
| Ar | 0.26 | 29 |
| Totals | 100.00 | 11208 |

The oxidation process can be applied in a manner such that it requires no net increase in power consumption by our invention. In fact, electric power could be produced from oxidation. The power required to produce and compress the oxidant (about 2 MW) is more than offset by the electric power which could be generated by utilizing the heat recovered in heat exchanger 88. For instance, by producing 1800 psia, 900° F. superheated steam from the 52.6 million Btu/h available in heat exchanger 88, over 6 MW of electric power can be produced.

Table VIII details the process streams in this example. Temperatures (T, °F.), pressures (P, psia), vapor fractions on a molar basis (Vap frac), and component flow rates in lb-mole/h are given.

TABLE VIII

|  |  |  |  | Component flow rate, lb-mole/h[#] | | | | | | | | | | |
| --- | --- | --- | --- | --- | --- | --- | --- | --- | --- | --- | --- | --- | --- | --- |
| Stream* | T, °F.[#] | P, psia[#] | Vap frac | $H_2$ | $N_2$ | CO | $CO_2$ | $H_2O$ | $O_2$ | Ar | $CH_4$ | $SO_2$ | $H_2S$ | COS | $CH_3OH$ |
| Streams from FIG. 1 | | | | | | | | | | | | | | | |
| 1 | 105 | 1110 | 1 | 16292 | 188 | 223 | 11578 | 39 | 0 | 205 | 57 | 0 | 204 | 14 | 0 |
| 2 | 134 | 1150 | 1 | 206 | 4 | 5 | 216 | 0 | 0 | 6 | 2 | 0 | 2 | 0 | 0 |
| 3 | 105 | 1100 | 1 | 16498 | 192 | 229 | 11793 | 39 | 0 | 211 | 59 | 0 | 207 | 14 | 0 |
| 5 | −29 | 1100 | 1 | 16227 | 184 | 217 | 945 | 0 | 0 | 190 | 48 | 0 | 2 | 0 | 0 |
| 7 | 50 | 1100 | 0 | 0 | 0 | 0 | 0 | 28 | 0 | 0 | 0 | 0 | 0 | 0 | 0 |
| 8 | 50 | 1100 | 1 | 16498 | 192 | 229 | 11793 | 11 | 0 | 211 | 59 | 0 | 207 | 14 | 0 |
| 10 | 50 | 1100 | 1 | 16498 | 192 | 229 | 11793 | 0 | 0 | 211 | 59 | 0 | 207 | 14 | 0 |
| 13 | −45 | 1100 | 1 | 16227 | 184 | 217 | 945 | 0 | 0 | 190 | 48 | 0 | 2 | 0 | 0 |
| 14 | 4 | 1100 | 0.987 | 16498 | 192 | 229 | 11793 | 0 | 0 | 211 | 59 | 0 | 207 | 14 | 0 |
| 24 | −21 | 1100 | 0.957 | 16349 | 188 | 224 | 7160 | 0 | 0 | 202 | 54 | 0 | 79 | 4 | 0 |
| 25 | −18 | 210 | 0 | 0 | 0 | 0 | 147 | 0 | 0 | 0 | 0 | 0 | 11 | 1 | 0 |
| 26 | −15 | 1100 | 1 | 16349 | 188 | 224 | 7160 | 0 | 0 | 202 | 54 | 0 | 79 | 4 | 0 |
| 27 | −55 | 1100 | 1 | 16245 | 185 | 218 | 2772 | 0 | 0 | 192 | 49 | 0 | 14 | 0 | 0 |
| 28 | −56 | 100 | 1 | 0 | 0 | 0 | 514 | 0 | 0 | 0 | 0 | 0 | 22 | 2 | 0 |
| 29 | −18 | 210 | 1 | 29 | 1 | 2 | 4309 | 0 | 0 | 5 | 3 | 0 | 115 | 9 | 0 |
| 30 | −56 | 100 | 1 | 30 | 2 | 3 | 3985 | 0 | 0 | 8 | 5 | 0 | 53 | 3 | 0 |
| 31 | −21 | 400 | 1 | 120 | 2 | 3 | 178 | 0 | 0 | 4 | 1 | 0 | 2 | 0 | 0 |
| 32 | −54 | 400 | 1 | 74 | 2 | 2 | 36 | 0 | 0 | 2 | 1 | 0 | 0 | 0 | 0 |
| 51 | −95 | 1100 | 1 | 16227 | 184 | 217 | 945 | 0 | 0 | 190 | 48 | 0 | 2 | 0 | 0 |
| 52 | −43 | 30 | 1 | 6 | 0 | 1 | 2339 | 0 | 0 | 2 | 2 | 0 | 34 | 2 | 2 |
| 53 | −91 | 400 | 1 | 12 | 0 | 0 | 2 | 0 | 0 | 0 | 0 | 0 | 0 | 0 | 0 |
| 54 | 60 | 50 | 0 | 0 | 0 | 0 | 0 | 0 | 0 | 0 | 0 | 0 | 0 | 0 | 2 |
| 74 | 88 | 1100 | 1 | 16227 | 184 | 217 | 945 | 0 | 0 | 190 | 48 | 0 | 2 | 0 | 0 |
| 77 | 158 | 1595 | 1 | 65 | 4 | 6 | 10632 | 0 | 0 | 15 | 9 | 0 | 203 | 14 | 2 |
| Internal stage streams from FIG. 1a: HP stage (stage 16) | | | | | | | | | | | | | | | |
| 35 | −15 | 1100 | 0 | 149 | 4 | 5 | 4633 | 0 | 0 | 9 | 4 | 0 | 128 | 10 | 0 |
| 38 | −21 | 400 | 0 | 29 | 1 | 2 | 4455 | 0 | 0 | 5 | 3 | 0 | 126 | 10 | 0 |
| 41 | −30 | 210 | 0.043 | 29 | 1 | 2 | 4455 | 0 | 0 | 5 | 3 | 0 | 126 | 10 | 0 |
| Internal stage streams from FIG. 1a: MP stage (stage 17) | | | | | | | | | | | | | | | |
| 35 | −55 | 1100 | 0 | 104 | 3 | 5 | 4388 | 0 | 0 | 10 | 5 | 0 | 65 | 3 | 0 |
| 38 | −54 | 400 | 0 | 30 | 2 | 3 | 4352 | 0 | 0 | 8 | 5 | 0 | 65 | 3 | 0 |
| 41 | −65 | 100 | 0.051 | 30 | 2 | 3 | 4498 | 0 | 0 | 8 | 5 | 0 | 76 | 5 | 0 |

TABLE VIII-continued

| Stream* | T, °F.[#] | P, psia[#] | Vap frac | Component flow rate, lb-mole/h[#] | | | | | | | | | | | |
|---|---|---|---|---|---|---|---|---|---|---|---|---|---|---|---|
| | | | | $H_2$ | $N_2$ | CO | $CO_2$ | $H_2O$ | $O_2$ | Ar | $CH_4$ | $SO_2$ | $H_2S$ | COS | $CH_3OH$ |
| Internal stage streams from FIG. 1b: LP stage (stage 50) | | | | | | | | | | | | | | | |
| 55 | −41 | 1250 | 0 | 0 | 0 | 0 | 113 | 0 | 0 | 0 | 0 | 0 | 8 | 1 | 1260 |
| 57 | −38 | 1100 | 0.915 | 16245 | 185 | 218 | 2885 | 0 | 0 | 192 | 49 | 0 | 22 | 1 | 1260 |
| 63 | −95 | 1100 | 0 | 19 | 1 | 1 | 1940 | 0 | 0 | 2 | 2 | 0 | 20 | 1 | 1260 |
| 66 | −91 | 400 | 0 | 6 | 0 | 1 | 1938 | 0 | 0 | 2 | 2 | 0 | 20 | 1 | 1260 |
| 69 | −104 | 30 | 0.066 | 6 | 0 | 1 | 2452 | 0 | 0 | 2 | 2 | 0 | 42 | 3 | 1260 |
| 70 | −43 | 30 | 0.634 | 6 | 0 | 1 | 2452 | 0 | 0 | 2 | 2 | 0 | 42 | 3 | 1260 |
| Streams from FIG. 2 | | | | | | | | | | | | | | | |
| 77 | 159 | 1610 | 1 | 65 | 4 | 6 | 10632 | 0 | 0 | 15 | 9 | 0 | 203 | 14 | 2 |
| 82 | 340 | 1350 | 1 | 0 | 6 | 0 | 0 | 0 | 381 | 14 | 0 | 0 | 0 | 0 | 0 |
| 84 | 390 | 1610 | 1 | 0 | 6 | 0 | 0 | 0 | 381 | 14 | 0 | 0 | 0 | 0 | 0 |
| 85 | 550 | 1610 | 1 | 65 | 4 | 6 | 10632 | 0 | 0 | 15 | 9 | 0 | 203 | 14 | 2 |
| 87 | 982 | 1595 | 1 | 0 | 10 | 0 | 10663 | 290 | 0 | 29 | 0 | 216 | 0 | 0 | 0 |
| 89 | 600 | 1595 | 1 | 0 | 10 | 0 | 10663 | 290 | 0 | 29 | 0 | 216 | 0 | 0 | 0 |
| 90 | 209 | 1595 | 0.985 | 0 | 10 | 0 | 10663 | 290 | 0 | 29 | 0 | 216 | 0 | 0 | 0 |
| 92 | 105 | 1595 | 0.975 | 0 | 10 | 0 | 10663 | 290 | 0 | 29 | 0 | 216 | 0 | 0 | 0 |
| 94 | 105 | 1595 | 0.975 | 0 | 10 | 0 | 10663 | 290 | 0 | 29 | 0 | 216 | 0 | 0 | 0 |

*Some stream numbers on FIGS. 1a and 1b are not shown because they are the same as streams on FIG. 1, as described in the Detailed Description. For instance, stream 14 on FIG. 1 represents stream 18 (not shown in the table above) on FIG 1a. Some stream numbers from FIG. 1a appear twice because they represent streams from two different stages - i.e. the stages denoted by numbers 16 and 17 on FIG. 1. Stream 77 appears twice, once as it appears in the Example described for FIG. 1, and once for a variation of the Example described for FIG. 2.
[#]Stream temperatures, pressures and molar flow rates by component are rounded to the nearest whole number.

What is claimed is:

1. A continuous process for removing acid gases from a syngas comprising a sequence of at least two stages, each stage comprising the steps of (a) condensing acid gases from the syngas by cooling the syngas by non-contact heat exchange to produce liquefied acid gases, (b) separating the liquefied acid gases from the syngas, and (c) evaporating the liquefied acid gases to provide the cooling of the syngas in step (a), with the stages in the sequence being designated stage 1 through stage N, the letter N representing the number of stages in the sequence, with each of the stages in the sequence cooling the syngas to a successively lower temperature as the syngas progresses from stage 1 to stage N, and each of the stages in the sequence evaporating the liquefied acid gases at successively lower pressures, said successively lower pressures being within a range of a maximum of about 800 psia to a minimum of about 6 psia, thereby separately producing an acid gas product stream from each of the stages, with stage N discharging a purified syngas, wherein at least two of the acid gas product streams from the stages are pressurized and then sequestered.

2. The process of claim 1 wherein the syngas contains water vapor and wherein the syngas is dried to a dewpoint temperature sufficiently low to prevent deposits of ice or hydrates in the process.

3. The process of claim 2 which further comprises the step of cooling the syngas before the syngas enters stage 1.

4. The process of claim 3 where N is 2 to 5.

5. The process of claim 4 wherein each of the stages comprises the steps of (a) condensing the acid gases from the syngas by cooling the syngas by non-contact heat exchange to produce the liquefied acid gases, (b) separating the liquefied acid gases from the syngas, and (c) evaporating the liquefied acid gases during the non-contact heat exchange to provide the cooling of the syngas in step (a).

6. The process of claim 5 where N is 2 and wherein unevaporated liquefied acid gases leave step (c) in stage 1 and are mixed with the liquefied acid gases of step (c) of stage 2.

7. The process of claim 5 where N is 3 and wherein unevaporated liquefied acid gases leave step (c) in stage 1 and are mixed with the liquefied acid gases of step (c) of stage 2, and further wherein unevaporated liquefied acid gases leave step (c) of stage 2 and are mixed with the liquefied acid gases of step (c) of stage 3.

8. The process of claim 5 where N is 4 and wherein unevaporated liquefied acid gases leave step (c) in stage 1 and are mixed with the liquefied acid gases of step (c) of stage 2, and further wherein unevaporated liquefied acid gases leave step (c) in stage 2 and are mixed with the liquefied acid gases of step (c) of stage 3, and further wherein unevaporated liquefied acid gases leave step (c) in stage 3 and are mixed with the liquefied acid gases of step (c) of stage 4.

9. The process of claim 5 where N is 5 and wherein unevaporated liquefied acid gases leave step (c) in stage 1 and are mixed with the liquefied acid gases of step (c) of stage 2, and further wherein unevaporated liquefied acid gases leave step (c) in stage 2 and are mixed with the liquefied acid gases of step (c) of stage 3, and further wherein unevaporated liquefied acid gases leave step (c) in stage 3 and are mixed with the liquefied acid gases of step (c) of stage 4, and further wherein unevaporated liquefied acid gases leave step (c) in stage 4 and are mixed with the liquefied acid gases of step (c) of stage 5.

10. The process of claim 5 where the coldest temperature in stage N is less than about −70° F. and where the syngas entering stage N is mixed with an antifreeze liquid and wherein stage N comprises the steps of (a) condensing acid gases from the syngas by cooling the syngas by non-contact heat exchange to produce a mixture of liquefied acid gases and antifreeze liquid, (b) separating the mixture of liquefied acid gases and antifreeze liquid from the purified syngas, and (c) evaporating the mixture of liquefied acid gases and antifreeze liquid during the non-contact heat exchange to provide the cooling of the syngas in step (a), and wherein an unevaporated mixture of antifreeze liquid and liquefied acid gases leaves step (c) and is recycled to the syngas entering stage N and wherein freezing of the liquefied acid gases is prevented by the antifreeze within stage N.

11. The process of claim 10 wherein the antifreeze liquid is an alcohol or a mixture of alcohols with a freezing point lower than about −110° F. and a normal boiling point higher than about 100° F.

12. The process of claim 11 wherein the antifreeze liquid is methanol.

13. The process of claim 5 wherein the liquefied acid gases leaving step (b) of each stage are flashed to release combustible gases dissolved in the liquefied acid gases.

14. The process of claim 13 where the combustible gases are recycled by pressurizing the combustible gases and where the pressurized combustible gases are mixed with the syngas before the syngas enters stage 1.

15. The process of claim 5 wherein the syngas is cooled before entering stage 1 by external refrigeration.

16. The process of claim 5 wherein heat is transferred from the syngas in between one or more of the stages to the purified syngas thereby cooling the syngas and warming the purified syngas.

17. The process of claim 16 wherein heat is transferred from the syngas before entering stage 1 to the purified syngas, thereby cooling the syngas and warming the purified syngas.

18. The process of claim 17 wherein the syngas is cooled before entering stage 1 by external refrigeration.

19. The process of claim 17 wherein the syngas is dried by condensing and separating water from the syngas and wherein after removing the condensed water the syngas is further dried to a dewpoint temperature sufficiently low to prevent deposits of ice or hydrates in the process.

20. The process of claim 5 wherein one or more of the acid gas product streams from the stages are oxidized by oxygen to convert sulfur in the acid gas product streams to sulfur dioxide or sulfur trioxide.

21. The process of claim 20 wherein the oxidized acid gas product streams are cooled by heating an external process stream.

22. The process of claim 21 wherein the oxidized acid gas product streams are pressurized and then sequestered.

23. The process of claim 10 where N is 2 and wherein unevaporated liquefied acid gases leave step (c) in stage 1 and are mixed with the liquefied acid gases of step (c) of stage 2.

24. The process of claim 10 where N is 3 and wherein unevaporated liquefied acid gases leave step (c) in stage 1 and are mixed with the liquefied acid gases of step (c) of stage 2, and further wherein unevaporated liquefied acid gases leave step (c) of stage 2 and are mixed with the liquefied acid gases of step (c) of stage 3.

25. The process of claim 10 where N is 4 and wherein unevaporated liquefied acid gases leave step (c) in stage 1 and are mixed with the liquefied acid gases of step (c) of stage 2, and further wherein unevaporated liquefied acid gases leave step (c) in stage 2 and are mixed with the liquefied acid gases of step (c) of stage 3, and further wherein unevaporated liquefied acid gases leave step (c) in stage 3 and are mixed with the liquefied acid gases of step (c) of stage 4.

26. The process of claim 10 where N is 5 and wherein unevaporated liquefied acid gases leave step (c) in stage 1 and are mixed with the liquefied acid gases of step (c) of stage 2, and further wherein unevaporated liquefied acid gases leave step (c) in stage 2 and are mixed with the liquefied acid gases of step (c) of stage 3, and further wherein unevaporated liquefied acid gases leave step (c) in stage 3 and are mixed with the liquefied acid gases of step (c) of stage 4, and further wherein unevaporated liquefied acid gases leave step (c) in stage 4 and are mixed with the liquefied acid gases of step (c) of stage 5.

27. The process of claim 10 wherein the liquefied acid gases leaving step (b) of each stage are flashed to release combustible gases dissolved in the liquefied acid gases.

28. The process of claim 27 where the combustible gases are recycled by pressurizing the combustible gases and where the pressurized combustible gases are mixed with the syngas before the syngas enters stage 1.

29. The process of claim 10 wherein the syngas is cooled before entering stage 1 by external refrigeration.

30. The process of claim 10 wherein heat is transferred from the syngas in between one or more of the stages to the purified syngas thereby cooling the syngas and warming the purified syngas.

31. The process of claim 30 wherein heat is transferred from the syngas before entering stage 1 to the purified syngas thereby cooling the syngas and warming the purified syngas.

32. The process of claim 31 wherein the syngas is cooled before entering stage 1 by external refrigeration.

33. The process of claim 31 wherein the syngas is dried by condensing and separating water from the syngas and wherein after removing the condensed water the syngas is further dried to a dewpoint temperature sufficiently low to prevent deposits of ice or hydrates in the process.

34. The process of claim 10 wherein one or more of the acid gas product streams from the stages are oxidized by oxygen to convert sulfur in the acid gas product streams to sulfur dioxide or sulfur tri oxide.

35. The process of claim 34 wherein the oxidized acid gas product streams are cooled by heating an external process stream.

36. The process of claim 35 wherein the oxidized acid gas product streams are pressurized and then sequestered.

37. The process of claim 11 wherein the antifreeze liquid is ethanol.

38. The process of claim 11 wherein the antifreeze liquid is propanol.

39. The process of claim 11 wherein the antifreeze liquid is isopropanol.

40. The process of claim 11 wherein the antifreeze liquid is butanol.

41. The process of claim 11 wherein the antifreeze liquid is isobutanol.

42. The process of claim 11 where N is 2 to 20.

* * * * *

UNITED STATES PATENT AND TRADEMARK OFFICE
CERTIFICATE OF CORRECTION

PATENT NO.         : 7,294,327 B2                                               Page 1 of 1
APPLICATION NO.    : 11/384279
DATED              : November 13, 2007
INVENTOR(S)        : Timmons S. McClanahan and Michael C. Crim It is certified that error appears in the above-identified patent and that said Letters Patent is hereby corrected as shown below:

Column 40, line 59, so that the reference in claim 42 "claim 11" reads --claim 1--

Signed and Sealed this

Thirteenth Day of May, 2008

JON W. DUDAS
*Director of the United States Patent and Trademark Office*